US012778683B2

(12) United States Patent
Signoretti et al.

(10) Patent No.: US 12,778,683 B2
(45) Date of Patent: Nov. 3, 2026

(54) SYSTEM AND METHOD FOR COMPUTER-AIDED SURGICAL NAVIGATION IMPLEMENTING 3D SCANS

(71) Applicant: Waldemar Link GmbH & Co. KG, Hamburg (DE)

(72) Inventors: Riccardo Signoretti, Jersey City, NJ (US); Louis-Francois Lapointe, Livingston, NJ (US); Jennifer Gass, Summit, NJ (US); Obinna Nwanna, Morristown, NJ (US); Raymond Bellon, Jersey City, NJ (US)

(73) Assignee: Waldemar Link GmbH & Co. KG, Hamburg (DE)

( * ) Notice: Subject to any disclaimer, the term of this patent is extended or adjusted under 35 U.S.C. 154(b) by 16 days.

(21) Appl. No.: 18/981,495

(22) Filed: Dec. 14, 2024

(65) Prior Publication Data

US 2025/0143802 A1 May 8, 2025

Related U.S. Application Data

(60) Division of application No. 17/731,220, filed on Apr. 27, 2022, now Pat. No. 12,201,380, which is a (Continued)

(51) Int. Cl.
*A61B 34/20* (2016.01)
*A61F 2/46* (2006.01)

(52) U.S. Cl.
CPC ............ *A61B 34/20* (2016.02); *A61F 2/4603* (2013.01); *A61F 2/4609* (2013.01); *A61B 2034/2048* (2016.02)

(58) Field of Classification Search
CPC ........... A61B 17/16–1659; A61B 17/17–1796; A61B 34/20; A61B 34/25;
(Continued)

(56) References Cited

U.S. PATENT DOCUMENTS 8,057,482 B2 * 11/2011 Stone .................. A61B 17/175 606/88
11,813,027 B2 * 11/2023 Link ...................... A61B 34/20
(Continued)

FOREIGN PATENT DOCUMENTS

WO WO-2016030512 A1 * 3/2016 ............ A61B 34/20

OTHER PUBLICATIONS

Communication Pursuant to Rule 164(2)(a) and Article 94(3) EPC mailed Jul. 31, 2024 in connection with European Patent Application No. 20823917.8, 11 pgs.
(Continued)

*Primary Examiner* — Eric S Gibson
(74) *Attorney, Agent, or Firm* — Chiesa Shahinian & Giantomasi PC

(57) ABSTRACT

A surgical navigation system for providing computer-aided surgery. The surgical navigation system includes a handheld surgical tool with computer-aided navigation, a graphical user interface module, and optionally an imaging device. The handheld surgical tool includes a handle that may comprise at least one sensor for detecting orientation of the. A computing device and at least one display device are associated with the handheld surgical tool and configured to display a target trajectory of the handheld surgical tool for the surgical procedure.

20 Claims, 27 Drawing Sheets

Related U.S. Application Data continuation of application No. PCT/IB2020/000867, filed on Oct. 28, 2020.

(60) Provisional application No. 62/926,657, filed on Oct. 28, 2019.

(58) Field of Classification Search
CPC .... A61B 2034/2048; A61B 2034/2065; A61B 2090/3764; A61F 2/46; A61F 2/4603; A61F 2/4607; A61F 2/4609; A61F 2/461; A61F 2/4612
See application file for complete search history.

(56) References Cited

U.S. PATENT DOCUMENTS

| | | | | |
|---|---|---|---|---|
| 12,201,380 | B2 * | 1/2025 | Signoretti | A61F 2/46 |
| 2005/0049486 | A1 * | 3/2005 | Urquhart | A61B 34/20 600/429 |
| 2008/0009697 | A1 * | 1/2008 | Haider | A61B 34/30 600/407 |
| 2010/0312247 | A1 * | 12/2010 | Tuma | A61B 17/175 606/89 |
| 2011/0301654 | A1 | 12/2011 | Wozencroft et al. | |
| 2012/0157887 | A1 * | 6/2012 | Fanson | A61B 34/25 600/595 |
| 2014/0135616 | A1 * | 5/2014 | Stein | A61B 17/92 600/424 |
| 2014/0135744 | A1 | 5/2014 | Stein et al. | |
| 2015/0287236 | A1 * | 10/2015 | Winne | A61B 1/00009 382/128 |
| 2016/0135762 | A1 * | 5/2016 | Mihailescu | A61B 6/547 600/424 |
| 2017/0165008 | A1 * | 6/2017 | Finley | A61B 6/4441 |
| 2017/0252110 | A1 * | 9/2017 | Link | A61B 34/20 |
| 2018/0012413 | A1 * | 1/2018 | Jones | G06F 3/0346 |
| 2018/0200002 | A1 * | 7/2018 | Kostrzewski | A61B 34/25 |
| 2018/0296283 | A1 * | 10/2018 | Crawford | A61B 17/7082 |
| 2018/0344301 | A1 * | 12/2018 | Wehrli | A61B 17/00 |
| 2019/0038366 | A1 * | 2/2019 | Johnson | A61B 90/98 |
| 2019/0053691 | A1 | 2/2019 | Hansen et al. | |
| 2019/0209154 | A1 * | 7/2019 | Richter | A61B 17/320068 |
| 2019/0231443 | A1 * | 8/2019 | McGinley | A61B 90/06 |
| 2019/0350657 | A1 * | 11/2019 | Tolkowsky | G06T 15/06 |
| 2019/0380789 | A1 * | 12/2019 | Link | A61B 34/20 |
| 2019/0380792 | A1 * | 12/2019 | Poltaretskyi | G06N 3/08 |
| 2022/0361955 | A1 * | 11/2022 | Signoretti | A61F 2/4603 |
| 2025/0107856 | A1 | 4/2025 | Signoretti et al. | |
| 2025/0143802 | A1 * | 5/2025 | Signoretti | A61F 2/46 |

OTHER PUBLICATIONS

Office Action mailed Mar. 5, 2026 in connection with U.S. Appl. No. 18/981,489, filed Dec. 14, 2024, 16 pgs.

* cited by examiner

410

601

410

601

410

410

601

SYSTEM AND METHOD FOR COMPUTER-AIDED SURGICAL NAVIGATION IMPLEMENTING 3D SCANS

CROSS-REFERENCE TO RELATED APPLICATIONS

This application in a Divisional of prior-filed U.S. Utility patent application Ser. No. 17/731,220, filed Apr. 27, 2022, which is a bypass Continuation of International Patent Application No. PCT/IB2020/000867, filed Oct. 28, 2020, which claims the benefit of priority to U.S. Provisional Patent Application No. 62/926,657, filed on Oct. 28, 2019; The disclosures of all of which are incorporated by reference in their entirety.

FIELD OF THE INVENTION

The invention relates to a surgical navigation system having a handheld surgical tool with computer-aided navigation. The handheld surgical tool comprises a housing, an instrument shaft, and a sensor unit. The surgical navigation system further comprises at least one imaging unit configured to generate a three-dimensional model/contour of an anatomical surface and a graphical user interface module configured to display the three-dimensional surface/contour and the location of the handheld surgical tool.

BACKGROUND

Orthopedic implantation procedures such as hip arthroplasty, knee arthroplasty, shoulder arthroplasty (TSA), and spine arthroplasty, can comprise two primary steps: a registration step, in which for the bone of interest the virtual frame of reference (for example, as provided by a camera) is matched with the actual frame of reference; and an implant targeting/placement step, in which the implant device is implanted into the patient. Proper positioning of surgical tools and implants, with respect to a patient's anatomy, is extremely important in order to ensure the best outcome. For example, in these implantation procedures, proper orientation of surgical guides, cutting tools, and implants is essential to ensure joint replacement functionality. Misalignment of the surgical guides, cutting tools, and/or implants can lead to detrimental consequences, such as joint dislocation, decreased joint motion and mobility, damage to surrounding tissue, long term pain, and early implant failure. For hip arthroplasty in particular, correct implant positioning may be challenging due to a variety of issues, as altered anatomy in revision cases, glenoid bone loss, and unreliable landmarks are commonly encountered in the patient population. In these cases, directing the glenoid baseplate along an appropriate axis with sufficient bone stock may be a difficult intra-operative task.

The ability to properly place the surgical guides, cutting tools, and implants is often difficult for surgeons, and even minor orientation changes can lead to improper implant alignment. Physical landmarks may be attached to the anatomy to guide and orient the surgeon during these procedures. However, such methods are imperfect and can lead to misalignment due to various reasons, such as there was an error in registering the position of the marker relative to the position of the bone; the marker is not secure and moves relative to the bone; or the camera is unable to detect the marker because of the presence of fluid or material from the surgery that can cover the marker. In instances when the surgeon does not attach markers but rather uses other physical features of the body for registration, errors can occur if those physical features are inaccurately measured or if the surgeon does not orient the patient's anatomy properly. And while three-dimensional reconstructions of computed tomography (CT) or magnetic resonance imaging (MRI) scans can improve surgical planning, recreating the same plan during surgery can be a demanding task.

In order to attempt to address at least some of the above problems, efforts have been made to develop technologies that can assist with proper placement of tools during surgery. For example, U.S. Pat. No. 8,057,482 B2 describes a handheld surgical tool with certain navigation features that are provided to improved positional accuracy. The tool features a button which must be pressed when the device achieves its basic reference position, which zeros the tool. Once this is accomplished, the tool can be freely manipulated by the surgeon, and it will show its positioning in space on three numerical displays provided at its casing. The displays show three-dimensional angular orientation of the tool in space. This device generally improves a surgeon's ability to determine positioning of the tool in an area with limited access, and consequently restricted visual observance. However, it can be rather difficult for the surgeon to control the plurality of displays in order to check whether a desired orientation has already been reached or is maintained. Moreover, the device is not configured to compare the location of the surgical tool to a desired orientation, nor is it configured to generate model(s) of the anatomy such that the surgeon can visualize placement of the surgical tool. Thus, the surgical tool according to U.S. Pat. No. 8,057,482 B2 does not adequately prevent misalignment of the surgical tool during a medical procedure.

Patient-specific instrumentation (PSI) has become popular in orthopedic subspecialties such as total hip, knee, and shoulder arthroplasty, pelvic and acetabular procedures, and spinal deformities, with varying degrees of success. However, PSI has the disadvantages of requiring a lead time of two or more weeks to receive the instrument before surgery, and during surgery it is not possible to modify the implant that was selected or its orientation.

Thus, there remains a need in the art for orthopedic implantation procedures that are reliable and reproducible, and that results in accurate positioning and alignment of the implant.

SUMMARY

Some of the main aspects of the present invention are summarized below. Additional aspects are described in the Detailed Description of the Invention, Example, and Claims sections of this disclosure. The description in each section of this disclosure is intended to be read in conjunction with the other sections. Furthermore, the various embodiments described in each section of this disclosure can be combined in various ways, and all such combinations are intended to fall within the scope of the present invention.

Accordingly, the disclosure provides a surgical navigation system for use in a patient, comprising (a) a handheld surgical tool with computer-aided navigation, wherein the handheld surgical tool comprises a handle and an instrument shaft; and (b) a graphical user interface (GUI) module, wherein the GUI module comprises at least one computing device and a visual display that is configured to indicate the location of the handheld surgical tool. In some embodiments, the surgical navigation system also comprises an imaging device.

The handle may comprise a processor and at least one sensor unit. The at least one sensor unit may comprise 3-axis accelerometer, a 3-axis rate gyroscope, a 3-axis magnetometer, or a combination thereof. In some embodiments, the at least one sensor unit is configured to generate orientational data of the handheld surgical tool.

The processor or the at least one computing device may be configured to determine the orientation of the handheld surgical tool based on the orientational data. In some embodiments, the processor or the at least one computing device is configured to compare the orientation of handheld surgical tool with at least one preset target orientation.

The visual display may be configured to indicate any deviation of the orientation of the handheld surgical tool from the at least one preset target orientation.

The imaging device may be configured to generate data that can be transformed into the three-dimensional image or contour. The imaging device may comprise a time-of-flight camera, a pair of stereoscopic cameras, or a three-dimensional scanning tool.

In some embodiments, the surgical navigation system may further comprise at least one marker that is attachable to a portion of the patient's anatomy, and in certain embodiments two markers that are each attachable to a different portion of the patient's anatomy. A marker engager can be attached to the handheld surgical tool, in which the marker engager is configured to engage with the one or more markers at a set orientation. The processor may be configured to detect an orientation of the one or more markers and, in some embodiments, configured to measure angular orientations and linear distances of anatomical features in relation to the one or more markers.

In some embodiments, the computing device is configured to generate a three-dimensional model or contour of a surface of the patient's anatomy or portion thereof. The three-dimensional model or contour may be generated based upon data from the imaging device.

In some embodiments, the GUI module is configured to receive data on one or more of location of the handheld surgical tool, deviation of the location of the handheld surgical tools from a desired location, images of the patient's anatomy or portion thereof, and a three-dimensional model of the patient's anatomy or portion thereof. In certain embodiments, the GUI module is configured to overlay one or more of: images of the patient's anatomy or portion thereof, the three-dimensional model of the patient's anatomy or portion thereof, the location of the handheld surgical tool, the desired location for the handheld surgical tool. In further embodiments, the GUI module is configured to display one or more of images of the patient's anatomy or portion thereof, the three-dimensional model of the patient's anatomy or portion thereof, the location of the handheld surgical tool, the desired location for the handheld surgical tool. In some embodiments, the GUI module is configured to display the overlay.

In embodiments of the invention, the GUI module is configured to qualitatively or quantitatively indicate the deviation between the location of the handheld surgical tool and the desired location of the handheld surgical device. The deviation may be indicated by one or more visual, aural, tactile or indications.

The surgical navigation system may be used in a method of implanting a prosthesis in a patient undergoing a joint arthroplasty. Further, the surgical navigation system may be used to improve the accuracy of prosthesis implantation in patient undergoing a joint arthroplasty. The joint arthroplasty may be hip arthroplasty, knee arthroplasty, or shoulder arthroplasty.

Accordingly, another aspect of the invention is directed to a method of implanting a prosthesis in a patient undergoing a joint arthroplasty using the surgical navigation system of the invention. The method may comprise (i) exposing the joint of the joint arthroplasty; (ii) placing one or more markers on anatomical features of the joint; (iii) engaging the handheld surgical tool with the one or more markers and recording orientation of the handheld surgical tool during the engagement; (iv) registering the orientation of the handheld surgical tool relative to the orientation of the joint; (v) displaying the orientation of the handheld surgical tool and a predetermined target orientation for the handheld surgical tool, on the visual display; and (vi) implanting the prosthesis using the handheld surgical tool and the visual display, wherein the orientation of the handheld surgical tool is adjusted according to the predetermined target orientation for the handheld surgical tool.

Alternatively, the method may comprise (i) exposing the joint of the joint arthroplasty; (ii) recording an image data of the anatomy of the joint, or a portion thereof, using the imaging device; (iii) generating a three-dimensional image or contour of the anatomy of the joint, or the portion thereof, using the GUI module; (iv) engaging the handheld surgical tool with the one or more anatomic features on the joint and recording orientation of the handheld surgical tool during the engagement; (v) registering the orientation of the handheld surgical tool relative to the orientation of the joint; (vi) displaying one or more of the three-dimension image or contour, the orientation of the handheld surgical tool, and a predetermined target orientation for the handheld surgical tool, on the visual display; and (vii) implanting the prosthesis using the handheld surgical tool and the visual display, wherein the orientation of the handheld surgical tool is adjusted according to the predetermined target orientation for the handheld surgical tool.

BRIEF DESCRIPTION OF THE DRAWINGS

The following description, given by way of example and not intended to limit the invention to the disclosed details, is made in conjunction with the accompanying drawings, in which like references denote like or similar elements and parts, and in which:

FIG. 8A shows the placement of the Cross-ASIS bar on the ipsilateral ASIS and the contralateral ASIS, and FIG. 8B shows the location of the ipsilateral ASIS and the contralateral ASIS on the pelvis.

FIG. 9A shows the placement of the Cross-ASIS bar on the ipsilateral ASIS and the pubis symphysis, and FIG. 9B shows the location of the ipsilateral ASIS and the pubis symphysis on the pelvis.

FIG. 12A illustrates placement of a first marker on the pelvis, and FIG. 12B illustrates engagement of the handheld surgical tool with the marker.

FIG. 13B illustrates repositioning of the leg to a neutral position.

FIG. 14A illustrates engagement of the handheld surgical tool with the second marker placed on the femur; and FIG. 14B illustrates using the handheld surgical tool to capture the femoral axis that is in line with the distal aspect of the femur.

FIG. 19A shows engaging the handheld surgical tool with the first marker in order to establish a reference point; FIG. 19B shows use of a cup impactor attached to the handheld surgical tool; and FIG. 19C shows how the visual display provides guidance to properly orient the cup impactor.

DETAILED DESCRIPTION OF THE INVENTION

Detailed embodiments of the present surgical navigation system, and corresponding methods, are disclosed herein. However, it is to be understood that the disclosed embodiments are merely illustrative of a surgical navigation system, and of methods, that may be embodied in various forms. In addition, each of the examples given in connection with the various embodiments of the systems and methods are intended to be illustrative, and not restrictive. Further, the drawings and photographs are not necessarily to scale, and some features may be exaggerated to show details of particular components. In addition, any measurements, specifications, and the like shown in the figures are intended to be illustrative, and not restrictive. Therefore, specific structural and functional details disclosed herein are not to be interpreted as limiting, but merely as a representative basis for teaching one skilled in the art to variously employ the present system and methods.

Surgical Navigation System

Figure 1:
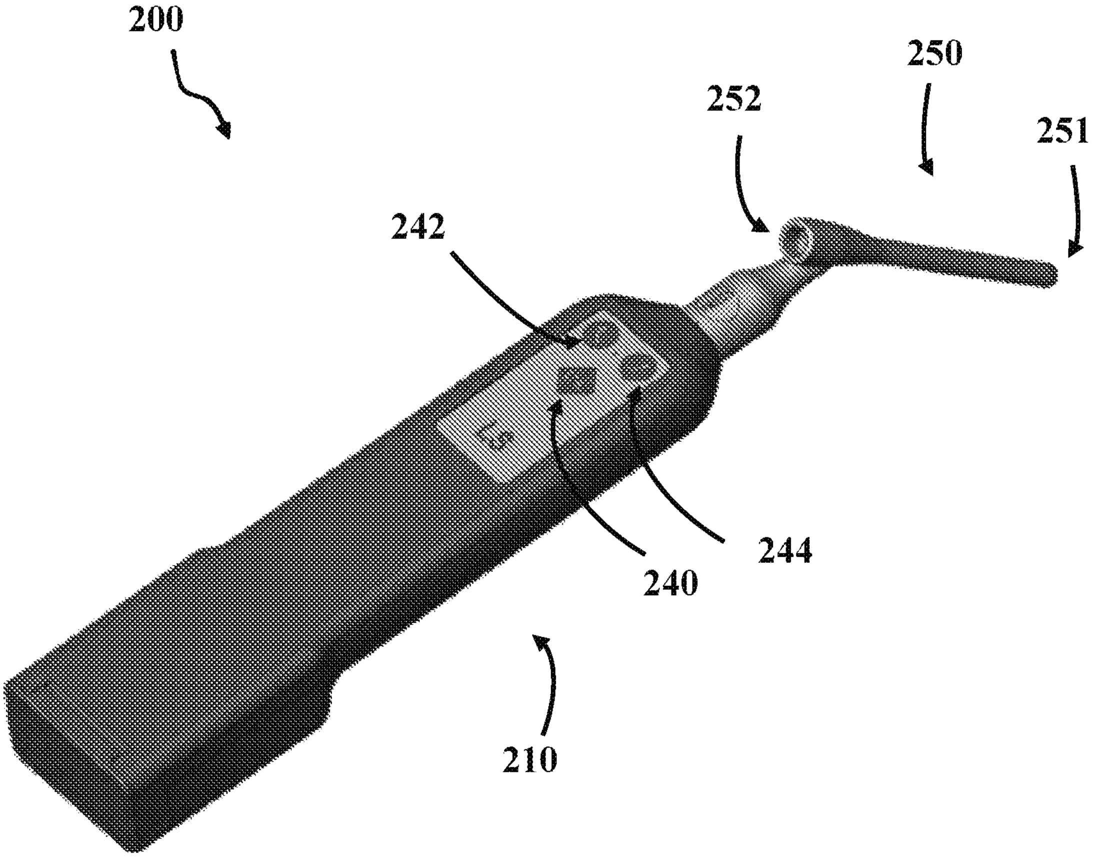
FIG. 1 illustrates a perspective view of a handheld surgical tool according to embodiments of the invention.

The surgical navigation system of the present invention comprises a handheld surgical tool and a graphical user interface (GUI) module, and, optionally, an imaging device. As shown in FIG. 1, the handheld surgical tool 200 may comprise a handle 210 and an instrument shaft or end tool 250. The GUI module 400 may comprise a computing device 405 and at least one visual display 410, and optionally at least one memory unit for storing data (see FIG. 2).

The instrument shaft 250 attaches to the proximal end of handle 210. The proximal end of handle 210 is configured to accommodate multiple different types of instrument shafts, for example, using a universal or common connection. The instrument shaft 250 includes a distal end tip 251 and a proximal end 252.

In some embodiments, the instrument shaft 250 may itself be a tool. In other embodiments, the instrument shaft 250 may be configured as an attachment point to receive a tool in an interchangeable fashion, such as a reamer, cutting jig, cup impactor, marker engager, an X-jig (as described herein), etc.

In certain embodiments, the instrument shaft 250 may be a guide having an internal hollow conduit for guiding a surgical instrument, and in order to place the surgical instrument in a correct manner, the surgical instrument may be placed with its tip on the target location in a certain orientation, which determines the angle with which the surgical instrument will interact with the target location.

Figure 2:
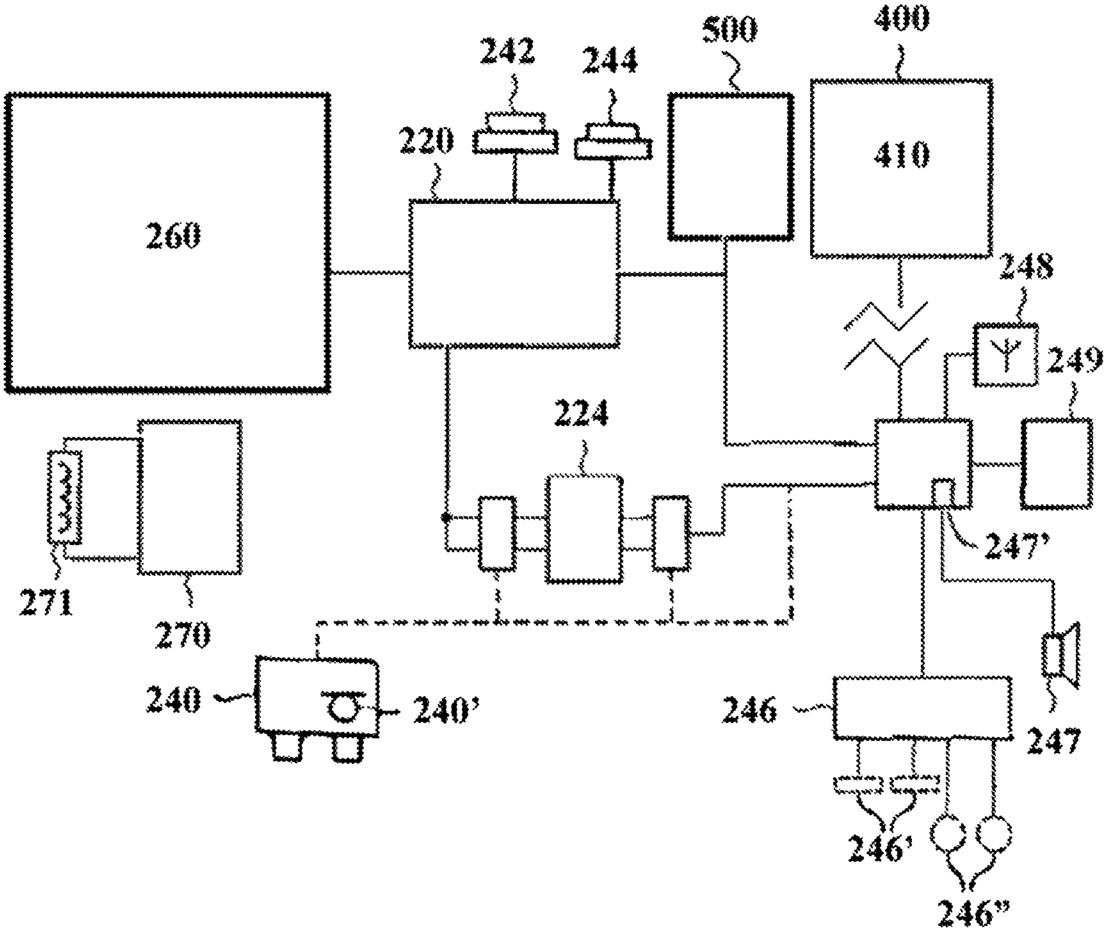
FIG. 2 illustrates function blocks of elements of a surgical navigation system according to embodiments of the invention.

The handle may comprise multiple components enclosed in a housing. For example, the handle may comprise a processor 220 and at least one sensor unit 260, (also known as an inertial measurement unit) as shown in FIG. 2. Optionally, the sensor unit may be a separate component, for example, in a sensor housing that can be attached to the handle.

The sensor unit 260 can provide orientational data of the handheld surgical tool. According to certain embodiments, the sensor unit 260 may comprise an inertial sensor in the form of a 3-axis accelerometer, a 3-axis rate gyroscope, a 3-axis magnetometer, or a combination thereof. In some embodiments, the sensor unit 260 may comprise a 3-axis accelerometer and 3-axis gyroscope. In certain embodiments, the sensor unit 260 may also comprise a temperature sensor. The processor 220 or the computing device 410 may be configured to determine the orientation of the handheld surgical tool 200 in space based on the orientational data from the sensor unit(s).

According to alternative embodiments, the sensor unit 260 may comprise other types of sensors configured to produce positional information. A data fusion module (not shown) may be configured to process the output signals of the sensor unit in a generally known manner (filtering, normalizing, calibrating, etc.) and, in some embodiments, to merge the processed signals in order to produce a unified consolidated position output signal. For this merging, generally known techniques may be used (for example, Kalman-filter, Quaternion-gradient, complementary filter, etc.). Optionally, the data fusion module is further configured to code the output by Quaternions in order to avoid singularities, such as gimbal lock issues. According to an alternative embodiment, the data fusion module may be incorporated into processor 220.

The consolidated output position signal of the data fusion module is supplied to processor 220. Based on this signal a conversion to Euler angles or three-dimensional vectors may be performed. In some embodiments, the output position signal includes data based on quaternions, which is subsequently converted to three-dimensional vectors and from there to 2D vectors. The position memory 224 is configured to store all positional data.

A set key 240 may be provided on the handle 210 of the handheld surgical tool 200 and used to calibrate the tool or store a current position of the tool. As an alternative to the set key 240, a microphone 240' may be provided, in which voice activation could be substituted for physically pressing the set key 240.

In embodiments of the invention, the processor 220 may be operatively connected to the position memory 224, the set key 240, and left control key 242 and right control key 244. The control keys may alter certain trajectories as well as provide a means for a user to interact with the GUI module 400 directly. Further, processor 220 may be configured to recall data from position memory 224.

According to certain embodiments, the processor 220 is configured for two operation modes, which may be selected by activation of the set key 240. In a first operation mode, the processor 220 is configured to recall stored incomplete position from position memory 224 generally, and to compare it against an actual position indication as supplied by the sensor unit(s) 261. Based on the difference between these position indications, the processor 220 generates a first deviation signal for one direction, such as inclination (or for another direction, such as anteversion). In the second operation mode, the processor 220 is configured to recall the full position indication and to compare it against the actual position indication as supplied by the sensor unit(s) 261. Based on the difference between these position indications it generates a different deviation signal that has one more dimension than the first deviation signal, such as inclination and anteversion in preferred embodiments. Switching from the first to the second operation mode may be controlled, in some embodiments, by the user by means of set key 240. Although certain embodiments herein describe the deviation signals being generated and supplied by processor 220, the invention is not so limited. For example, processing of positional data may be carried out by the GUI module, the handheld surgical tool, or combinations thereof.

The deviation signals are supplied to, or in some embodiments generated by, the GUI module 400 of the surgical navigation system. The GUI module 400 may comprise a computing device 405 and at least one visual display 410, and optionally at least one memory unit for storing data (for example, positional data from the handheld surgical tool 200). In some embodiments, the GUI module 400 may be configured to indicate direction and position—and in a qualitative and/or quantitative manner, magnitude—of any deviation as defined by the deviation signals. The GUI module 400 may also include a visual indicator, the visual indicator being formed by a visual display 410. The visual display 410 forming the visual indicator, according to embodiments, comprises a bullseye display within a crosshair pattern (see FIG. 3). According to some embodiments, and as shown in FIG. 2, the GUI module 400 may be in communication with the handheld surgical tool 200. For example, the GUI module 400 may communicate wirelessly with handheld surgical tool 200 via wireless transmitters 248, 249.

According to some embodiments, the handheld surgical tool 200 may include a tactile indicator 246, an aural indicator 247, a visual indictor (not shown), or combinations thereof. The tactile indicator 246 may comprise two pairs of vibration transducers 246' and 246" arranged on opposite lateral sides of the housing 210 and on the top and bottom side of the housing 210, respectively. As an aural indicator, a loudspeaker 247 may be provided, which is driven by a sound module 247' forming a part of either the handheld surgical tool 200 or the GUI module 400. The visual indictor may be in the form of a display, such as an LCD display, or can take the form of one or more lighting devices, such as LEDs.

Further, the handheld surgical tool 200 may be configured with a wireless transmitter 248 that is configured for communication with a wireless transmitter 249 on the GUI module 400. According to certain embodiments, the tactile indicator 246, aural indicator 247, and/or visual indictor may replace visual display 410. In such embodiments, the bullseye display within a crosshair pattern may be omitted, and rather, the handheld surgical tool 200 may provide the indication of direction and position, such as via audio cues provided by aural indicator 247.

A rechargeable or disposable battery 270 may be provided that supplies the various components of the handheld surgical tool via supply lines (not shown). In order to recharge the battery 270, a recharging coil 271 may be provided which is configured for wireless charging.

Figure 3:
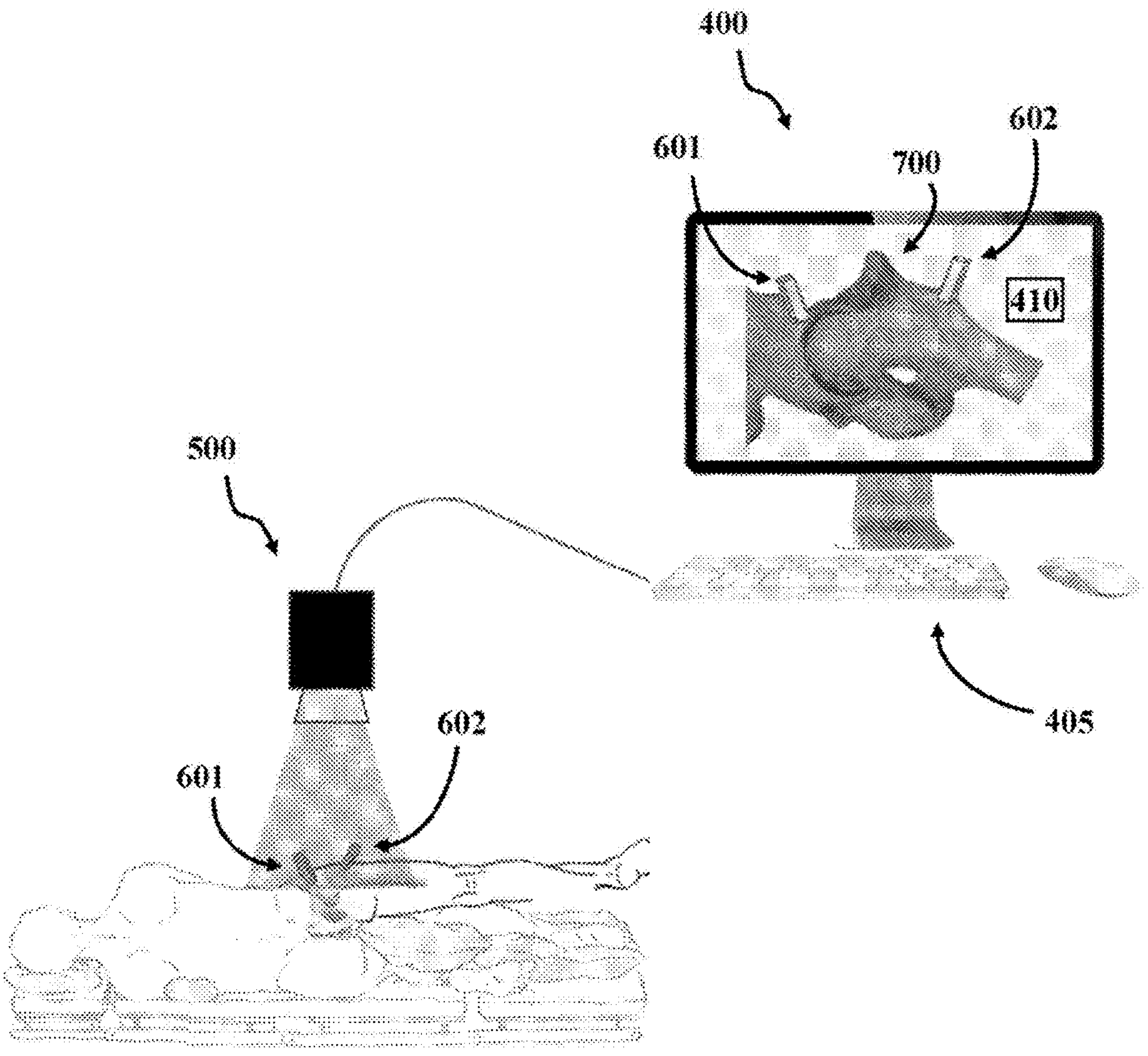
FIG. 3 illustrates components of a surgical navigation system according to embodiments of the invention.

The imaging device 500 of the surgical navigation system is configured to image portions of the anatomy in order to generate imaging data that is used to create three-dimensional surface(s)/contour(s), as shown in FIG. 3. According to certain embodiments, the imaging device 500 is integrated or otherwise attached to the handheld surgical tool 200. According to alternative embodiments, the imaging device 500 is a separate device and is configured to communicate with handheld surgical tool 200 and/or GUI module 400.

In some embodiments, the surgical navigation system may comprise a processor, having instructions stored on a non-transitory computer readable medium, that when executed by the processor, cause the processor to operate in two distinct operating modes, wherein in one of the two distinct operating modes a reduced position indication is processed. The reduced position indication is a position indication which lacks at least one indication for one degree of freedom compared to the full position indication of the second operating mode. For example, in Euclidean space three angle indications can be used to describe an orientation of a device in a three-dimensional space. But if the absolute location does not need to be monitored, then two, instead of three, of the angles may be monitored, which will not provide a fully fixed orientation, but will instead retain one degree of freedom. If, for example, angles for roll, pitch and yaw are used, then an incomplete position indication could only have indications of roll and yaw, leaving pitch as a degree of freedom. As another example, if only two rather than three angles are to be used (e.g., if roll is to be ignored), a full position indication will have both angles (e.g., pitch and yaw), whereas an incomplete position indication would indicate only one angle (e.g., yaw only). Detailed embodiments implementing the two operating modes, which are incorporated herein, are further described in co-pending U.S. patent application Ser. No. 16/442,155. Additionally, and with specific reference to hip arthroplasty applications, the angles may be the cup inclination and anteversion.

Methods of Using the Surgical Navigation System

The surgical navigation system of the present invention may be used in methods of implanting a prosthesis in a patient undergoing a joint arthroplasty, and methods of improving the accuracy of prosthesis implantation in a patient undergoing a joint arthroplasty.

For such methods, the surgical navigation system can be set up within the operating room. In order to do so, and as illustrated by FIG. 3, imaging device 500 may be located next to the patient that is on an operating table.

In embodiments in which the sensor unit 260 is to be attached to the handle 210, the handheld surgical tool 200 may be assembled. According to these embodiments, the handle 210 of handheld surgical tool 200 is sterile packed. The sterile pouch is opened, a lid is removed from the back of the handle 210, and the sensor unit 260 is inserted until fully engaged and flush with the handle 210. The lid may then be closed, sealing the sensor unit 260 within the handle 210.

A desired instrument shaft 250 (i.e., end tool) is chosen and attached to the proximal end of handle 210.

The handheld surgical tool 200 may be activated. By way of example only, removal of a pull tab on handheld surgical tool 200 will enable battery 270 to power on the components handheld surgical tool 200. Alternatively, a switch may be pressed to power on components handheld surgical tool 200.

In some embodiments, the handheld surgical tool 200 may undergo initialization. During initialization, the handheld surgical tool 200 measures the direction of gravity using its sensor unit 260, such that the position in space of the handheld surgical tool 200 is established against a coordinate system. In some embodiments, the handheld surgical tool 200 must remain motionless during initialization. An indicator may show that initialization is complete. An example of an indicator includes, but is not limited to, a light-emitting diode (LED) light, such as a green LED light.

The term "position in space" and its short form "position" in context of the present invention generally refers to a system with six degrees of freedom that may comprise absolute location and orientation. The location might be represented as coordinates of a three-dimensional space with perpendicular axes (e.g. X, Y, Z), while the orientation might be provided by Euler angles (e.g., yaw, pitch, and roll; alpha $\alpha$, beta $\beta$, and gamma $\gamma$; phi $\varphi$, theta $\theta$, and psi $\psi$) or by quaternions. In preferred embodiments, the coordinate system of the handheld device will be established relative to gravity, such that the y-axis is oriented opposite to the direction of gravity.

By means of definition, a coordinate system for the human body may be defined featuring an X-axis as side to side (left to right, right to left, i.e., lateral-medial direction), a Y-axis as up and down (feet to head, head to feet, i.e., superior/cranial-inferior/caudal direction), and a Z-axis (front to back, back to front, i.e., anterior/ventral-posterior/dorsal direction) orthogonal to the X- and Y-axis indicating depth. Alternatively, the coordinate system for the human body may be such that the Y-axis is opposite the direction of gravity; as a result, the alignment of the coordinate system compared to the human body will depend on the position of the patient. For example, if the patient is lying down on his/her back with the head towards the right, the Y-axis will align with the anterior/ventral-posterior/dorsal direction, the X-axis will align with the superior/cranial-inferior/caudal direction, and the Z-axis will align with the lateral-medial direction.

The imaging device 500 may image the relevant anatomy of the patient. The connection (for example, wireless) between the handheld surgical tool 200 and the GUI module 400 may be activated (for instance, by keying in a code indicated on the handheld surgical tool 200), and the connectivity may be verified (for example, by moving a part of the handheld surgical tool 200) by confirming that a corresponding icon (for example, a handle icon) on visual display 410 moves at the same time.

Aspects of the procedure (for example, surgical level, implant side, cup size, etc.) may be pre-stored or provided to the GUI module 400 and/or handheld surgical tool 200. For instance, based on provided aspects of the desired surgical procedure, default values for starting target angles appropriate for the intended surgery can be inputted. The GUI module 400 and/or handheld surgical tool 200 is programmed with these default target angle values and/or distance values for arthroplasty component positioning (for example, from research, published sources, or preoperative imaging data), for each type of surgery, that approximate the angles with which the surgical tool will need to be oriented for an effective surgery. This eliminates or minimizes the amount of adjustment (in other steps, described below) needed to establish a trajectory for the actual surgery—such as by allowing the initial trajectory to be within a crosshair on the visual display 410 of the GUI module 400.

Figure 4:
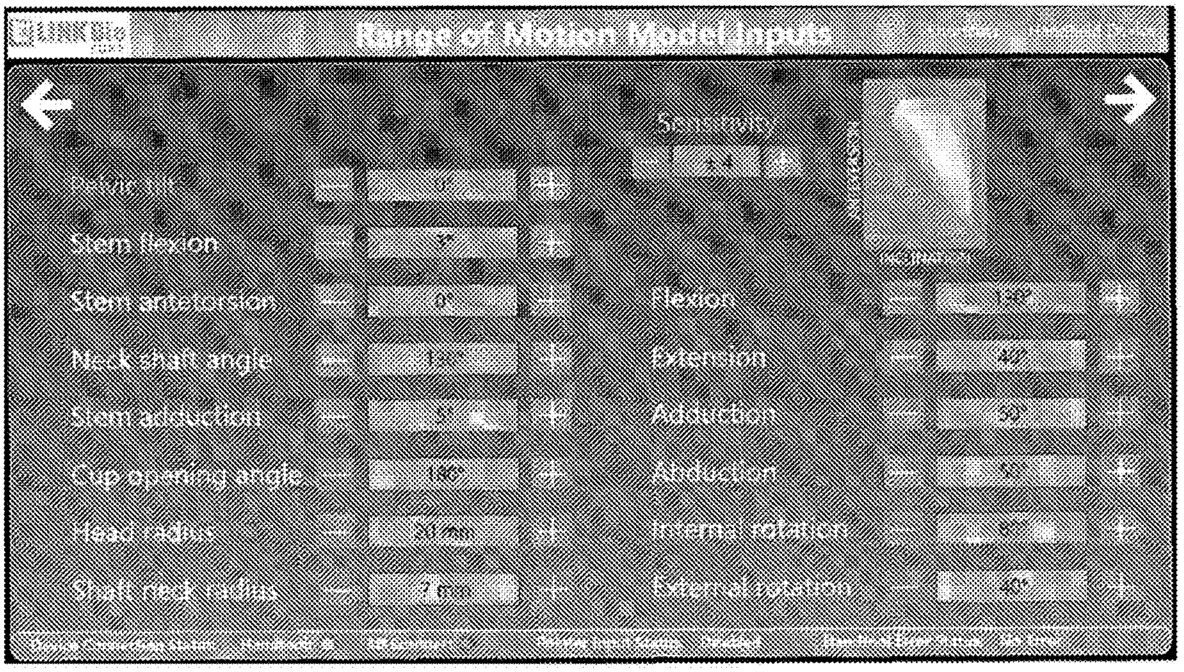
FIG. 4 illustrates an example of range of motion model inputs shown on a visual display according to embodiments of the invention.

By way of an example, for a hip arthroplasty, a "Range of Motion model" may be chosen as the cup replacement model, and the visual display 410 of the GUI module 400 may appear as shown in FIG. 4, which indicates that the desired post-operative range of motion of the patient, the geometric parameters of the implant, and the patient's pelvic tilt are required as inputs. The Range of Motion model is configured to generate a "heatmap" of cup orientations defined by anteversion and inclination angles based on the inputs. The heatmap will show, for example by using a green color, where the orientations will result in impingement-free motion.

According to embodiments, and as exemplified in FIG. 3, one or more markers may be placed on a portion of the patient's anatomy corresponding to the location of the surgical procedure, i.e., on one or more of the bones involved in the joint arthroplasty. The markers may be designed to engage with the handheld surgical tool 200. In preferred embodiments, a tool such as a marker engager 610 may be attached to the handheld surgical tool 200, for example at the distal end tip 251 of the handheld surgical tool 200.

In some embodiments, a first marker 601, such as a bone screw, is placed on a bone forming part of the joint. In some embodiments, the first marker 601 may have a unique shape and the marker engager 610 attached to the handheld surgical tool 200 may have a complementary shape, such that the first marker 601 and the marker engager 610 can mate in a single orientation. This allows for the marker engager 610 to fit with, over (or within) the first marker 601 in a specific orientation. Once placed, the marker engager 610 is mated to the first marker 601, and then the handheld surgical tool 200 is zeroed/calibrated to this position (for example, by pressing set key 240, or by a surgical team member or representative clicking a button on GUI module 400). The location of the first marker 601 may be previously established by the system (for example, via detection in a three-dimensional surface/model 700) of the anatomy, and as such the location of the handheld surgical tool 200 is similarly known. In this way, zeroing of the location of handheld surgical tool 200 within the navigation field can be effectuated. This also allows for the generation of positional information of the first marker 601 and the handheld surgical tool 200 relative to it.

The marker engager 610 may then be removed from the first marker 601 and brought in contact with one or more other features of the anatomy so as to capture a horizontal vector. The location of the handheld surgical tool 200 at this position is then stored, for example, by depression of set key 240. With this positional information, the relative position of the first marker 601 to the horizontal vector 301 is determined.

In some embodiments, a second marker 602 (similar to or the same as the first marker 601) can be placed on another portion of the patient's anatomy, depending upon the surgical procedure, such as on another bone that forms part of the joint. Once both the first marker 601 and the second marker 602 are placed the patient is repositioned such that a neutral position is achieved.

In some embodiments, similar to the first marker 601, the marker engager 610 attached to the handheld surgical tool 200 is mated to the second marker 602, and then the handheld surgical tool 200 is zeroed/calibrated to this position. The location of the second marker 602 may be previously established by the system (e.g., via detection in a three-dimensional surface/model 700) of the anatomy. The marker engager 610 may then be removed from the second marker 602 and brought in contact with one or more other features of the anatomy so as to capture a horizontal vector. The location of the handheld surgical tool 200 at this position is then stored.

In some embodiments, the imaging device 500 may image the relevant patient anatomy, including the first marker 601 and, if present, the second marker 602. In some embodiments, the imaging device 500 may be a three-dimensional scanning tool, which captures data corresponding to the shape/surface of the bone on which the marker(s) are located, as well as the location and orientation of the marker(s). Such data may be captured by moving the scanning tool around the relevant areas of the bone and capturing imaging data during the movement.

A processor (for instance, the processor of the handheld surgical tool, the processor of the GUI module, etc.) may obtain the imaging data and generate a three-dimensional surface/model of the anatomy and the marker(s). It is to be noted that three-dimensional surface/model only needs to be a representation of the relevant portion of the anatomy being scanned and does not need to be a representation of the entire anatomical structure. The processor, having instructions stored on a non-transitory computer readable medium, that when executed by the processor, cause the processor to detect relevant features of the anatomy from the three-dimensional surface/model with the aid of the marker(s). The processor may also calculate relevant orientations (for example, angular orientations) and distances with regards to the patient's anatomy. Such information may help add precision in determining how the bone should be modified for surgery (for example, where the bone should be cut, shaved, etc.).

In some embodiments, the process of attaching markers and scanning described herein may be repeated as necessary. For example, in some embodiments additional markers may be attached to different bones or anatomical features.

In alternative embodiments of the invention, markers are not attached to the bone or other anatomical features and, instead, the handheld surgical tool 200 is placed next to the target anatomy of the patient. The imaging device then images the target anatomy (for example, the hip) along with the handheld surgical tool 200. From this imaging data the location of the handheld surgical tool 200 is detected by the processor. The handheld surgical tool 200 can be calibrated to the navigation space based upon this information.

In some embodiments, the surgery may require cutting or removing a portion of bone. Using positional information that has been captured, the visual display 410 can indicate where, for example, a cutting jig is to be placed such that it properly aligns with particular anatomic features so that the location and angle of the cut is accurate.

In certain embodiments, the distal end 251 of the instrument shaft 250 of the handheld surgical tool 200 can be placed in real space at the starting point, such as within or on a marker in order to establish a starting reference point for the procedure. In preferred embodiments, the starting point may be registered on GUI module as a point in the virtual space of the system (for example, preferably, X=0, Y=0, Z=0; that is, the starting point is preferably set as the origin point in the virtual space of the system). Also, a proximal end 252 of the instrument shaft 250 may be registered as a point in the virtual space of the system relative to the starting point in the virtual space of the system, so that the orientation of the instrument shaft 250 in real space relative to the starting point in real space, and relative to the default target angle/trajectory/orientation, is determinable and representable by the system in the virtual space of the system. The handheld surgical tool 200 can be moved in real space to angulate the instrument shaft 250 about the starting point in real space until the visual display 410 indicates that the orientation of the shaft in real space relative to the starting point is aligned with the default target angle/trajectory/orientation.

For example, a predefined trajectory may be recalled from an associated memory (for instance, positional memory 224) and the handheld surgical tool 200 can be moved in real space and a position of an indicator on visual display 410 (for example, a green dot representing the proximal end 252 of the instrument shaft) is shown relative to a position of a target point (for example, the distal end tip 251 corresponding to the center of a bullseye's cross-hairs), and when the positions are aligned, the system has determined that the instrument shaft 250 is oriented in real space, relative to the predefined trajectory (for example, an established trajectory based on the literature or preoperative imaging data), and the display 410 alerts the user to the alignment (for example, by changing the GUI module color to predominantly green). According to certain embodiments, the predefined trajectory is based upon pre-planned inclination/anteversion, etc., as determined by the surgeon. According to alternative embodiments, patient images may be used as an input to validate the predefined trajectory. If the predefined trajectory is satisfactory, the surgical procedure is then effectuated (for instance, reaming or cutting of the bone).

In addition, a three-dimensional surface/contour 700 can be generated and displayed on visual display 410 showing the relevant anatomy, the instrument shaft 250 of the handheld surgical device 200, and the handheld surgical device 200. The visual display 410 may also indicate, on the image or three-dimensional surface/model, the angle of the orientation of the shaft (for example, by a line along the longitudinal axis of the shaft). Additionally, visual display 410 presents a relative angle/trajectory/orientation indicator changeable in virtual space (for example, a line rotatable in virtual space within the three-dimensional surface/model about the starting point 256, corresponding to the location of distal end tip 251). The user can change the angle/trajectory/orientation of the indicator in virtual space from the default angle/trajectory/orientation (foe instance, referencing anatomic landmarks shown on the image or in the three-dimensional surface/model) using the control keys 242 and 244, directly on GUI module 400, or by other suitable means. For example, if the user sees that indicator is not properly oriented in relation to the acetabulum, the user can change the angle/trajectory/orientation of the indicator until the line passes through the desired anatomy.

In preferred embodiments, the user can confirm the desired angle/trajectory/orientation, for example, by pressing set key 240. For instance, when the user determines that is at the appropriate angle/trajectory/orientation, the user can press set key 240. Upon confirmation, the target angle/trajectory/orientation is changed from the default angle/trajectory/orientation (for example, that was taken from research and literature sources) to the desired angle/trajectory/orientation (for example, that has been established by the user). Data for the new target angle/trajectory/orientation (i.e., for the desired angle/trajectory/orientation) is then saved into position memory 224. The data for the new target angle/trajectory/orientation may additionally or alternatively be stored in position memory housed externally to the housing of the handheld surgical tool 200—for example, in a separate device like a separate computer, hard drive, etc. This then locks in the desired angle/trajectory/orientation.

The handheld surgical tool 200 can be angulated and the visual display 410 can provide an indication of the location of handheld surgical tool 200, and indicate when the tool is aligned with the new, desired angle/trajectory/orientation. Preferably, when the positions are aligned, the handheld surgical tool 200 is maintained in real space in the aligned position, and the site is prepared (for instance, the surgeon reams the acetabulum, places an acetabular cup, etc.). At any time during the procedure, imaging can be used to check the accuracy of the chosen three-dimensional trajectory/orientation/position.

According to further embodiments, initial default angle/trajectory/orientation values may be based upon direct targeting. The initial three-dimensional trajectory/orientation/position can be determined by attaching hardware (for instance, fixation pins) to the target anatomy and then determining the trajectory/orientation at which the hardware is attached. For example, the system can capture the digital trajectory/orientation of a manually placed instrument or implant. According to traditional surgical methods when targeting for implant delivery, it is not uncommon to provisionally place a trial implant, guidewire, temporary fixation pin, drill bit, or the like, and take a radiograph to assess the positioning of the provisional placement in relation to known landmarks. In a fully manual environment, the surgeon would need to make an analog adjustment, such as, for example, the final implant placement should be oriented a few degrees more lateral and a few degrees upward. This process is arbitrary, error laden, requires a high level of spatial orientation awareness, and can result in misjudgments and improperly placed hardware. The surgical navigation system 100 can improve upon this process. The instrument shaft 250 of the handheld surgical 200 can be placed over a provisionally directed trial, guidewire, fixation pin, or the like, and the system can capture the digital orientation in real time, allowing the surgeon to more accurately adjust the final placement. According to an illustrative example, a temporary element (for instance, trial acetabular cup) is implemented. Instrument shaft 250 is then attached (or placed against) this fixation element. Once aligned, the three-dimensional trajectory/orientation of shaft 250 can be registered (for instance, by pressing the set key 240). Thereafter the shaft can be removed. Imaging device 500 then acquires first imaging data (for instance, allows for the creation of a first three-dimensional surface/model), which depicts the patients anatomy and the fixation element (or alternatively, X-rays of the relevant anatomy may be taken to observe the fixation element). Similar to the process described above, the registered trajectory/orientation from the initial alignment of the device provides an indication for this registered trajectory/orientation. Using control keys 242 and 244 (or the GUI module), a target trajectory/orientation can be modified, until a desired trajectory/orientation is obtained, which can then be locked-in (for instance, by using the set key 240). Finally, the shaft 250 of tool 200 is placed at the surgical site, and visual display 410 may display a bullseye type display (as exemplified in FIG. 3 to guide proper alignment of instrument shaft 250.

Once the bone is cut/reamed or otherwise modified according to the procedure, a new three-dimensional contour/surface 700 may be generated, which is based upon image data generated by imaging the bone including any markers. Updated calculations determining angles and positioning of, for instance, implant devices, can help identify where any adjustment to the implant devices are needed.

Figure 5:
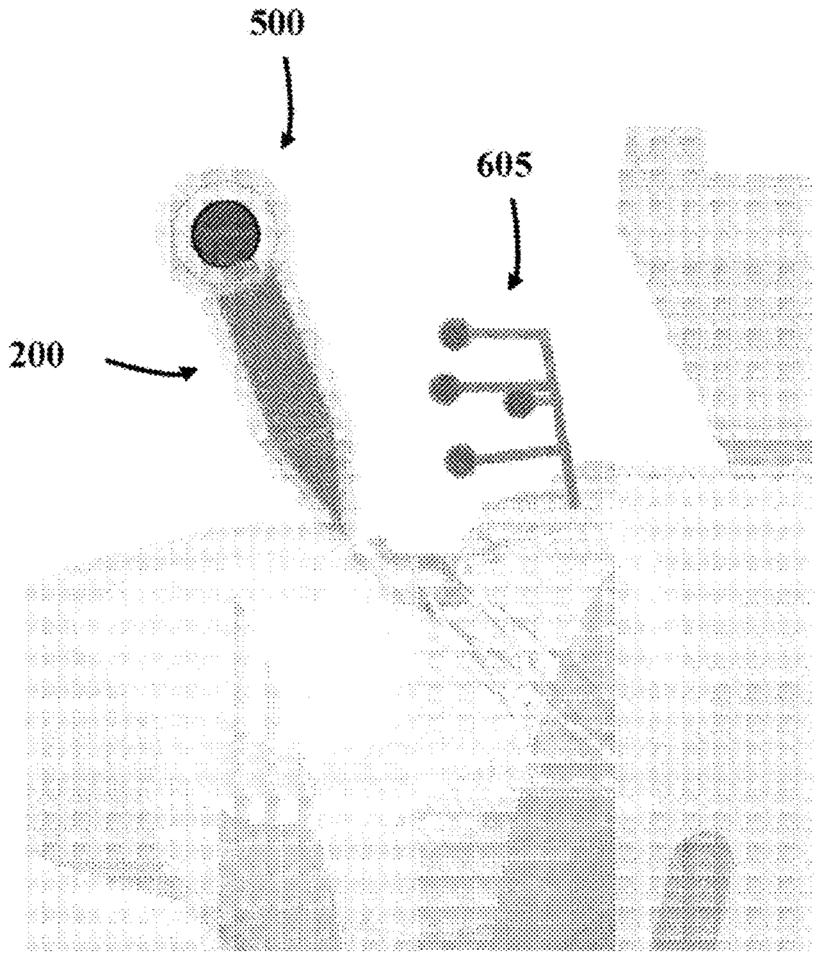
FIG. 5 illustrates components of a surgical navigation system in which an imaging device 500 is integrated with, or otherwise attached to, the handheld surgical tool, according to embodiments of the invention.

According to further embodiments, imaging device 500 may be integrated with, or otherwise attached to the handheld surgical tool 200, as illustrated by FIG. 5. In these further embodiments handheld surgical tool 200 may include sensor units 261, and communicate with GUI module 400. According to a variation thereof sensor units 261 as well as markers may be omitted. For example, with an integrated imaging device, the relative orientation of the handheld surgical tool 200 is fixed in relation to the imaging device 500. Thus, movements of the handheld surgical tool 200 are experienced by the imaging device 500. Accordingly, positional sensors do not need to measure the relative movement of the handheld surgical tool 200 and instead the imaging data itself can be used to detect movement of the handheld surgical tool 200. It is noted that a marker 605 may be placed on the anatomy in order to aid in orienting the handheld surgical tool 200.

Imaging device 500 may also be configured to project an image into the patient. For example, according to certain embodiments, imaging device 500 project a line beam (such as via laser projection) onto a bone to visually indicate a cut location. Such embodiments may include a motorized head which allows imaging device 500 to be rotated/moved. Additionally, or alternatively, such an image may be projected onto the three-dimensional surface/contour 700.

Hip Arthroplasty

In embodiments of the invention, the surgical navigation system of the present invention may be used for performing a hip arthroplasty. In particular, the surgical navigation system of the present invention may be used to achieve correct implant positioning.

In some embodiments, the hip arthroplasty may comprise a pre-planning step, in which different aspects of registration and/or implantation may be set. For example, settings for placement of the acetabular cup may include selection of a cup placement model that will be used for implanting the cup at a desired orientation; a reference plane that will be used for determining the desired cup orientation; and whether to include a final cup orientation measurement.

The cup replacement model may be selected from a Range of Motion model or an Extended Lewinnek model. The Range of Motion model involves application of an algorithm to calculate an impingement-free zone of cup orientations based on a target range of motion set, the patient's pelvic tilt, and the 3D angular neck and stem orientation within the femur (Hsu J et al., *J. Biomech.,* 82:193-203, 2018). The Extended Lewinnek model defines the "Lewinnek Safe Zone" (Lewinnek G E et al, *J. Bone Joint Surg. Am.,* 60-A: 217-220, 1978) as the target zone, but applies specific input information.

The reference plane may be selected from the anterior pelvic plane or the coronal plane. The anterior pelvic plane is an anatomic plane defined by the two anterior superior iliac spines (ASIS) and the midpoint of the pubic tubercles. The coronal plane is a functional plane and is defined as any vertical plane that divides the body into ventral and dorsal sections.

In some embodiments, the pre-planning step may also include selecting whether to detect a change in leg length. If selected, different aspects of the leg position can be measured before and after implantation, including leg length, mediolateral offset, and anteroposterior position, to determine what changes, if any, occurred. The selection may include recording the initial orientation of the femur so that the femur can be returned to the same orientation when performing the post-operative measurements.

To perform registration of the patient coordinate system, i.e., to establish the relationship between the virtual frame of reference of the joint (including orientation of the handheld surgical device 200) and the actual frame of reference of the joint (e.g., the actual orientation of the joint), the handheld surgical tool may be used to capture vectors that correspond to an anatomical plane of the patient. Each vector is captured by recording the orientation of the handheld surgical tool (i.e., recording the current quaternion of the handheld surgical device) and the vector is constructed from the recorded quaternion. In preferred embodiments, at least two vectors, corresponding to two planes, are captured.

Figure 6A:
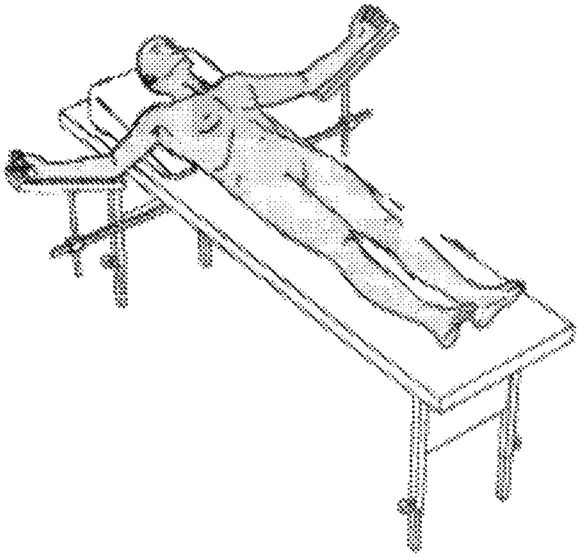
FIGS. 6A and 6B illustrate the supine (FIG. 6A) and lateral decubitus (FIG. 6B) positions, in which the patient may lie during a hip arthroplasty.
Figure 6B:
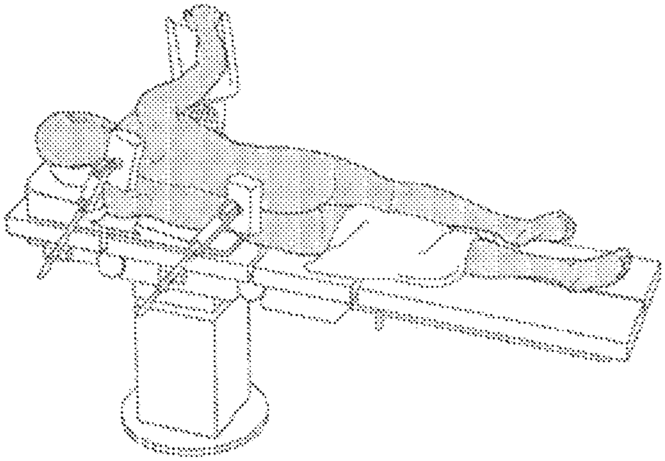
Figure 7:
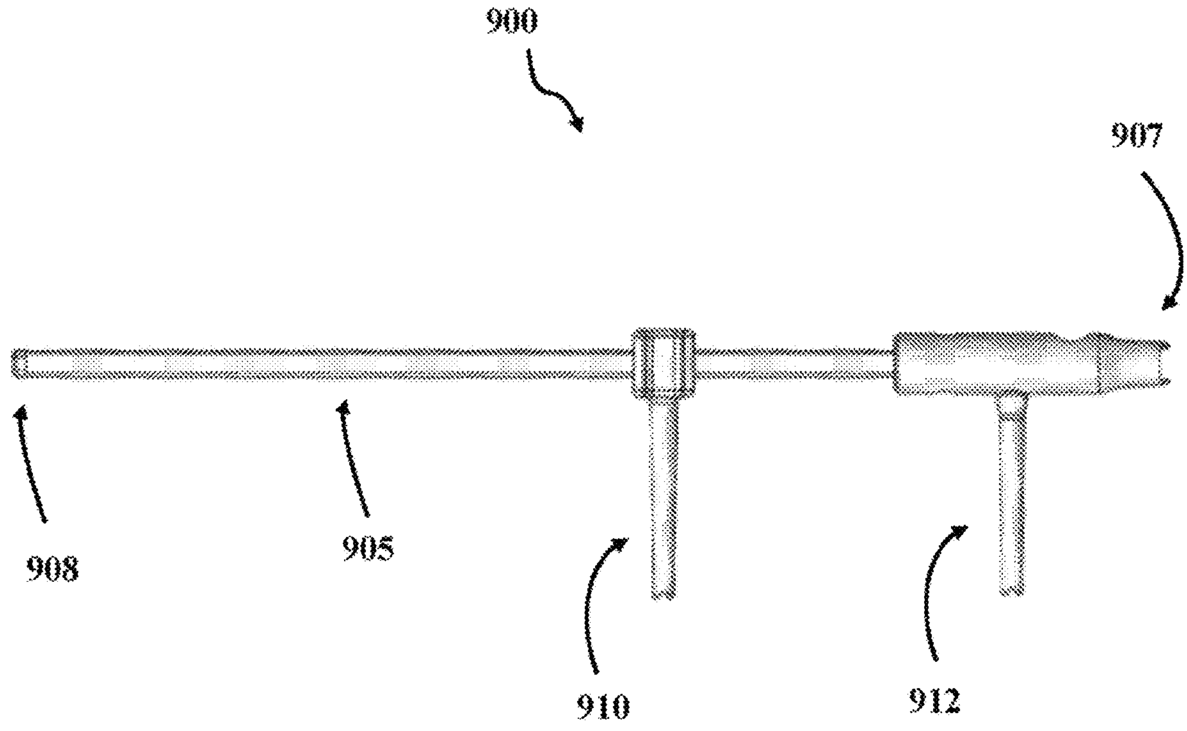
FIG. 7 illustrates a Cross-anterior superior iliac spine (ASIS) bar according to embodiments of the invention.
Figure 8A:
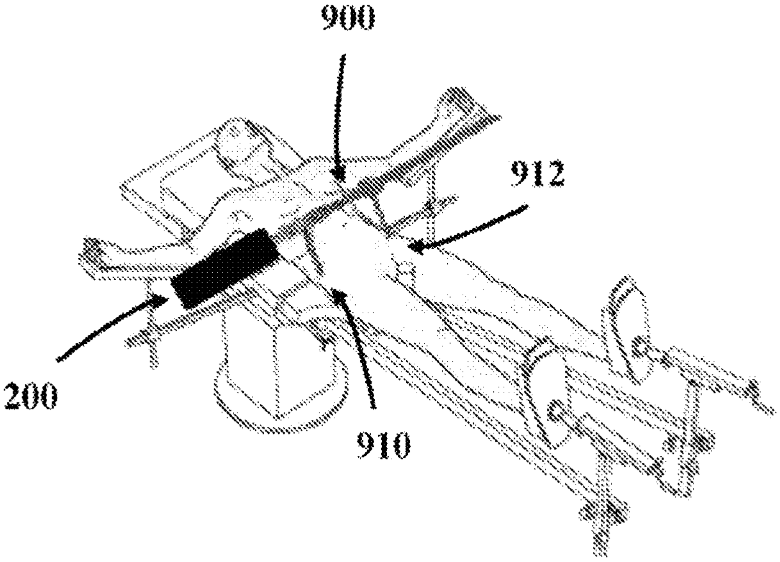
FIGS. 8A and 8B illustrate use of the Cross-ASIS bar according to embodiments of the invention.
Figure 8B:
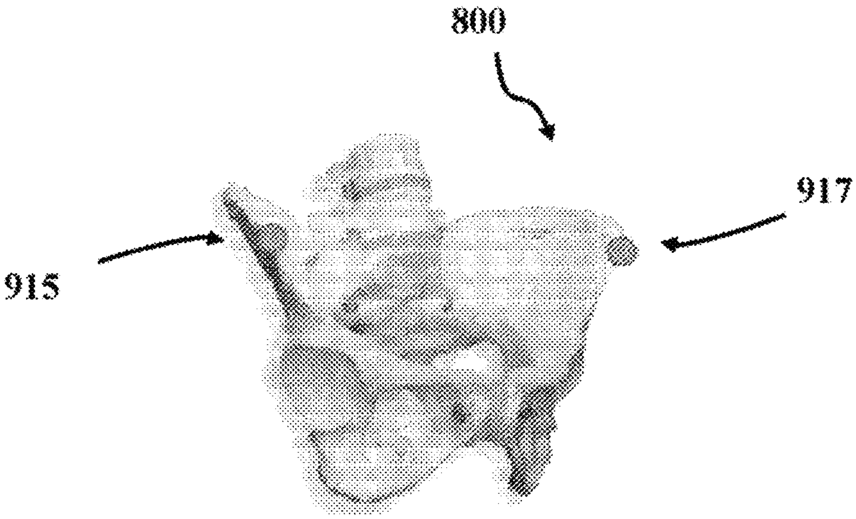

Different vectors may be captured depending on the position of the patient, i.e., whether the patient is in a supine position (see FIG. 6A) or in a lateral decubitus position (see FIG. 6B). If the patient is in a supine position, the handheld surgical tool 200 can capture the sagittal plane and the anterior pelvic plane. In some embodiments, a tool, such as a Cross-ASIS bar 900, may be used. As shown in FIG. 7, the Cross-ASIS bar 900 comprises a bar 905 having a proximal end 907 and a distal end 908, in which the proximal end 907 of the Cross-ASIS 900 is configured to engage with the distal end tip 251 of the handheld surgical tool 200. The Cross-ASIS bar 900 further comprises a first foot 910 and a second foot 912 that extend in the same direction from the bar 905 and are perpendicular to the long axis of the bar 905. The Cross-ASIS bar 900 is attached to the handheld surgical tool 200, so that the orientation of the handheld surgical tool 200 can be recorded when the Cross-ASIS 900 bar is identifying a plane. To register a sagittal plane, the first foot 910 is placed on the ipsilateral ASIS 915 (i.e., ipsilateral to the operative hip) and the second foot 912 is placed on the contralateral ASIS 917, and the resulting quaternion of the handheld surgical device is recorded (see FIG. 8). From this quaternion, the vector can be constructed.

In some embodiments, this vector pointing in the direction of the long axis of the cross-ASIS bar may be projected onto the coronal plane of the patient. The coronal plane of the patient in supine position may be assumed to be the same as the plane perpendicular to the direction of gravity, which is detected automatically when the handheld device is powered on, and is used to define the Y-axis of the surgical handheld device 200; as a result, no correction for the Y-axis is needed. The handheld-device-to-patient adjustment quaternion may be defined as the rotation between the unit X-axis and the inter-ASIS vector in handheld device coordinates projected onto the coronal plane. In some embodiments, these measurements are performed while the operating table remains perpendicular to the direction of gravity (i.e., horizontal).

Figure 9A:
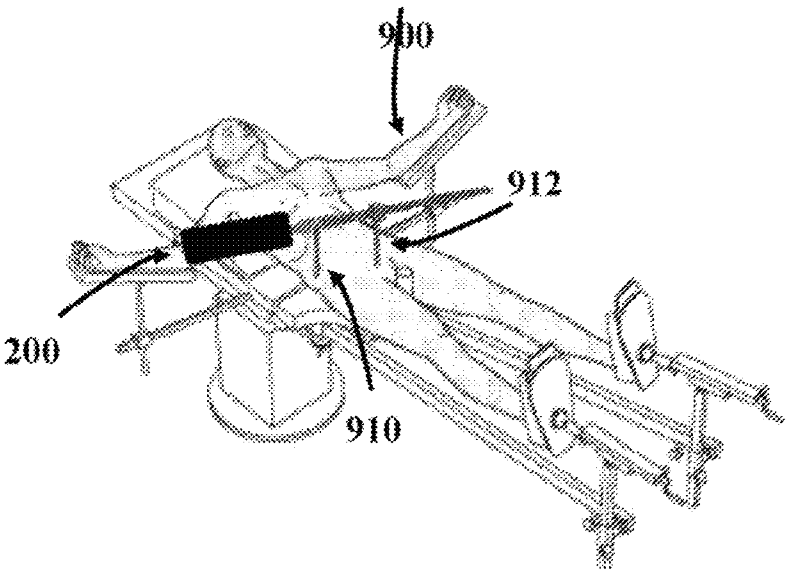
FIGS. 9A and 9B illustrate use of the Cross-ASIS bar according to embodiments of the invention.
Figure 9B:
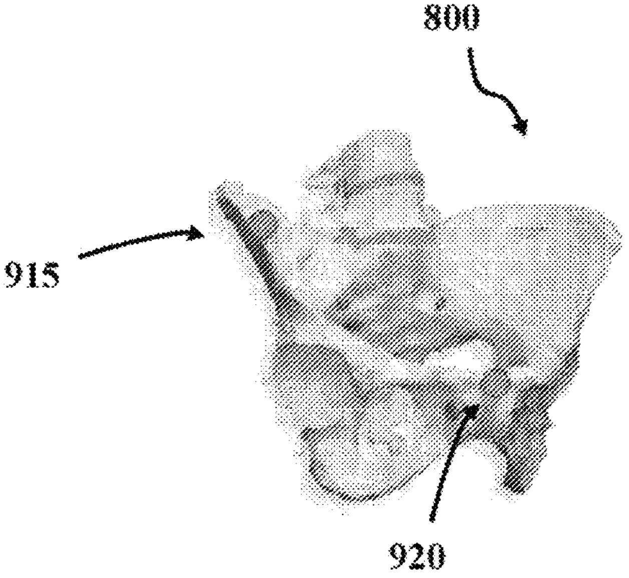

To register the anterior pelvic plane, two vectors are captured. The first vector is the same vector as recorded for registering the sagittal plane, but after recording the first vector, the Cross-ASIS bar can be pivoted such that the first foot 910 remains on the ipsilateral the Cross-ASIS bar and the second foot 910 is moved to the pubis symphysis 920 of the ipsilateral pelvis (see FIG. 9). The vector is captured in this pivoted position, and then both vectors can be used to identify and register the anterior pelvic plane. This also registers the pelvic tilt. The pelvic tilt is the angle between the vector in patient coordinates given by the long axis of the Cross-ASIS bar projected onto the sagittal plane and the positive Z-axis. When the pelvic tilt is not zero, the angles of inclination and anteversion subsequently reported are adjusted to the pelvic frame of reference.

Figure 10A:
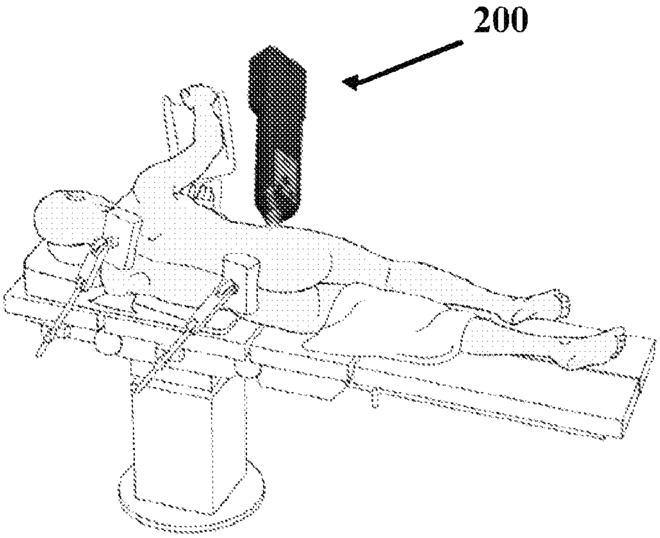
FIGS. 10A and 10B illustrate use of the handheld surgical device to register the front plane according to embodiments of the invention.
Figure 10B:
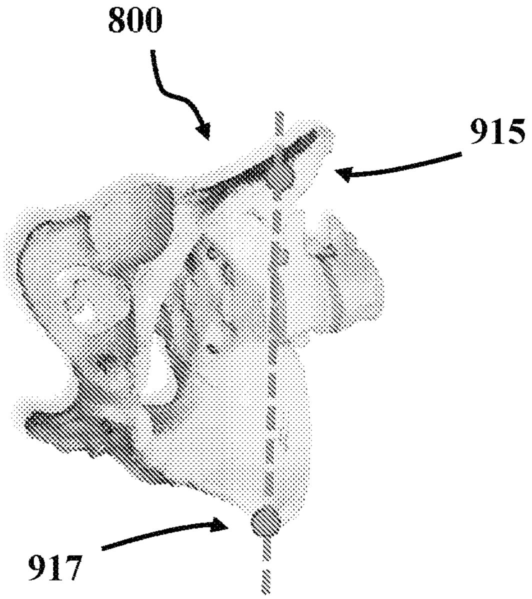
Figure 11A:
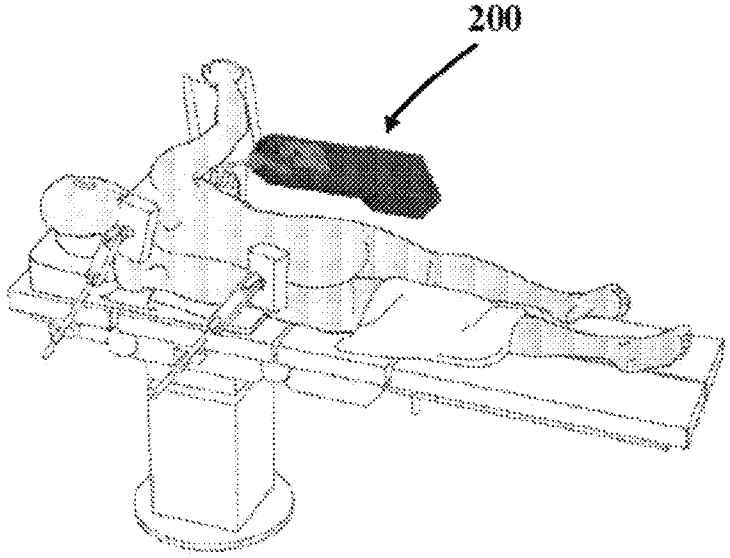
FIGS. 11A and 11B illustrate use of the handheld surgical device to register the horizontal plane according to embodiments of the invention.
Figure 11B:
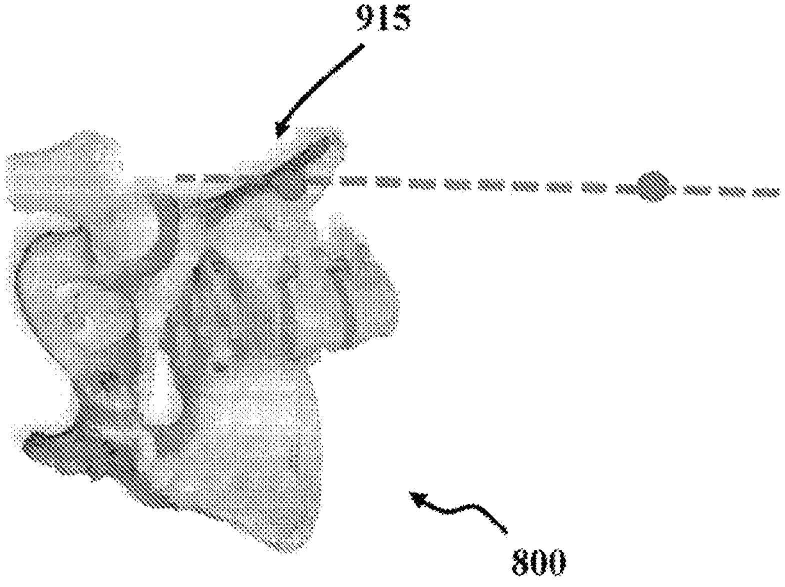

If the patient is in a lateral decubitus position, the handheld surgical tool 200 can be used to capture a frontal (coronal) plane and a horizontal plane. As shown in FIG. 10, the front plane can be registered by recording the vector created when the handheld surgical tool vertical across the ASIS and it assumes that the patient is perfectly lateral and orthogonal to the floor. The horizontal plane can be registered by recording the vector created when the handheld surgical tool is aligned with the main axis of the patient (see FIG. 11).

In some embodiments, recordation of the handheld surgical device during this registration step generates a handheld surgical device-to-patient adjustment quaternion In embodiments of the invention, one or more markers may be installed on the pelvis and/or femur. The markers may be installed by a manual method (using a mallet or similar instrument to tap the end of the marker into the bone and then screwing the marker until it is fully in the bone) or a power method (using a drill or the like to install the marker). A drill can also be used to create a pilot hole before installing the marker by the manual method or before screwing in the marker.

Figure 12A:
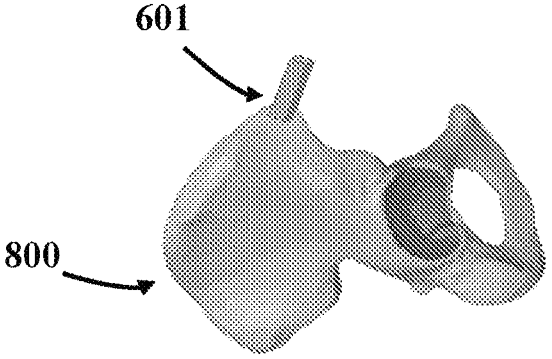
FIGS. 12A and 12B illustrate components of a surgical navigation system during an operating step, according to embodiments of the invention. In particular.
Figure 12B:
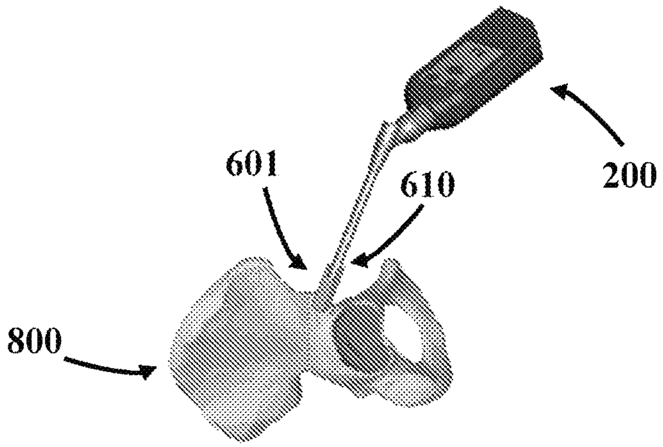

In some embodiments, a first marker 601 can be attached to the pelvis 800 as demonstrated in FIG. 12A. In preferred embodiments, the first marker 601 is attached on the superior-anterior rim of the acetabulum. A marker engager attached to the handheld surgical tool 200 may be mated to the first marker 601 and then the orientation of the handheld surgical tool 200 engaged with the first marker 601 may be recorded to generate positional information of the first marker 601 relative to the handheld surgical tool 200 (see FIG. 12B). In some embodiments, this positional information may be referred to as the recorded marker engagement quaternion.

The recorded marker engagement quaternion and handheld surgical device-to-patient adjustment quaternion can be used to construct two vectors in patient coordinates that define the pelvic marker orientation: one vector directed along the marker engagement axis and one vector perpendicular to define the roll. Mathematically, the engagement quaternion from the handheld device is adjusted to patient coordinates by computing the Hamiltonian product: $q_{engagement,patient}=q_{handtool\ to\ patient}*q_{engagement,handtool}$. Two orthogonal axes of the patient are rotated by this quaternion to obtain the marker engagement axis and roll vector.

Figure 13A:
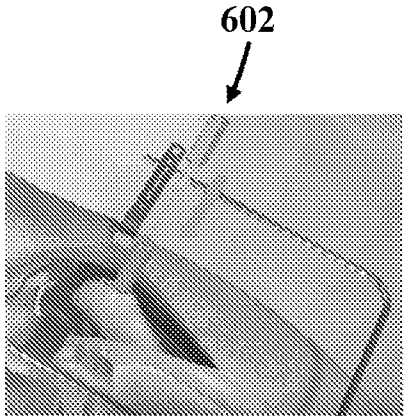
FIGS. 13A and 13B further illustrate components of a surgical navigation system during an operating step, according to embodiments of the invention. In particular, FIG. 13 A illustrates placement of a second marker on the femur.
Figure 16:
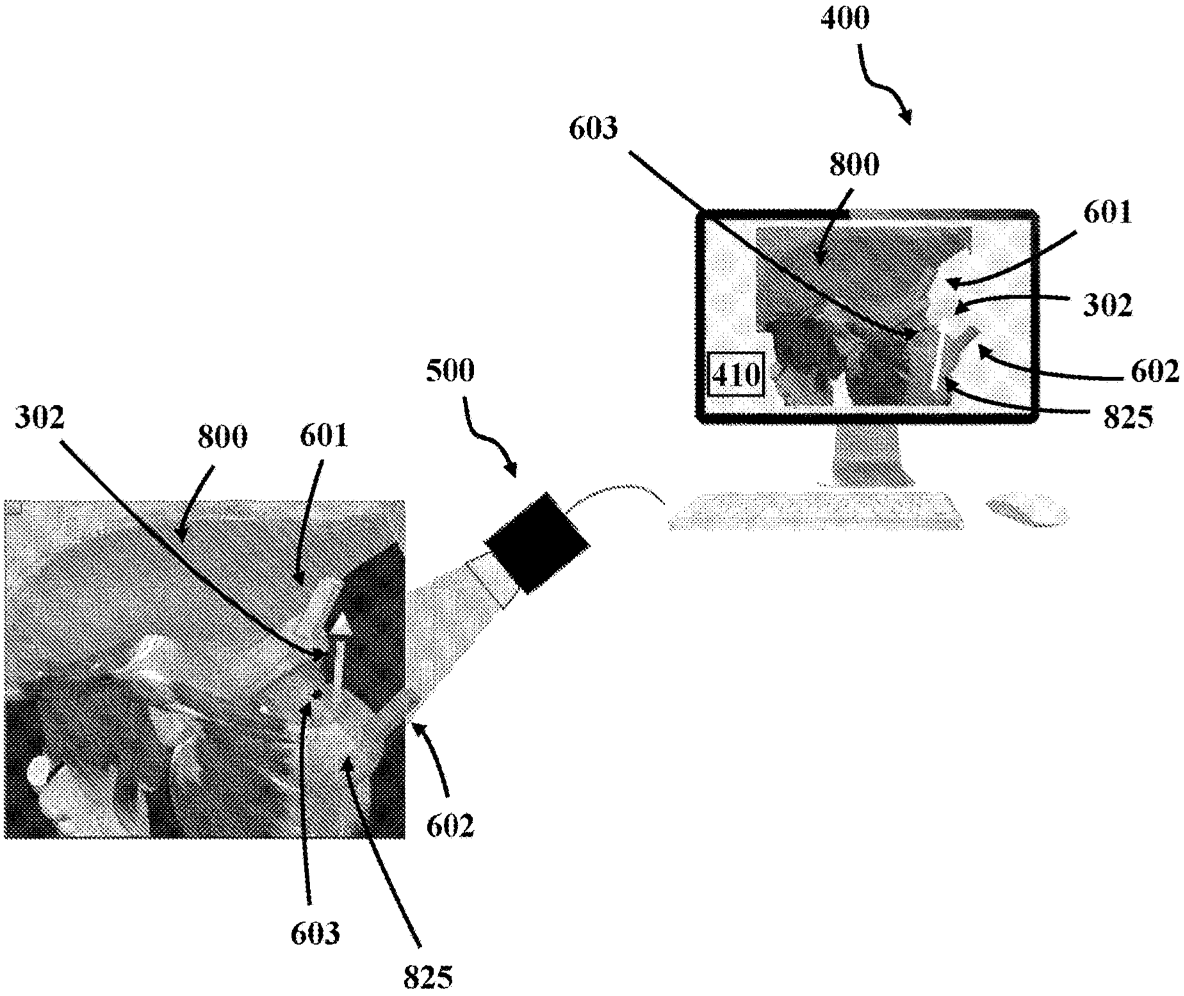
FIG. 16 illustrates components of a surgical navigation system during a further operating step according to embodiments of the invention, in which an imaging device images the relevant patient anatomy.

A femoral resection is performed, which may include broaching the femur in-situ. According to some embodiments, after the femur 825 is properly exposed, and as illustrated by FIGS. 13, 14, and 16, a second marker 602 (for example, a bone screw) can be placed on the femur 825, and in particular, on the greater trochanter (see FIG. 13A). A marker engager 610 attached to the handheld surgical tool 200 can be engaged with the second marker 602 (see FIG. 14A). Second marker 602 may have a unique shape, while the marker engager 610 has a complementary shape, such that they can mate in a single orientation. This allows for the marker engager 610 to fit with, over, or within, second marker 602 in a specific orientation. Once placed, the marker engager 610 is mated to second marker 602, and then the position of the handheld surgical tool 200 is recorded (for example, by pressing set key 240, or by a surgical team member or representative clicking a button on GUI module 400). Because the location of the second marker 602 is previously established by the system (for example, via detection in the three-dimensional surface/model 700), the location of the handheld surgical tool 200 is similarly known. The marker engager 610 may then be removed from the second marker 602 and, in some embodiments, the handheld surgical tool 200 may be brought in contact with lateral aspect of the greater trochanter, so as to capture femoral axis 302, which is a straight line in line with the distal aspect of the femur 825 (see FIG. 14B). The position of handheld surgical tool 200 may be stored, for example, by depressing set key 240. With this positional information, the relative position of the second marker 602 to femoral axis 302 is determined, and the relative angle of the horizontal axis 301 to femoral axis 302 is determined.

Figure 13B:
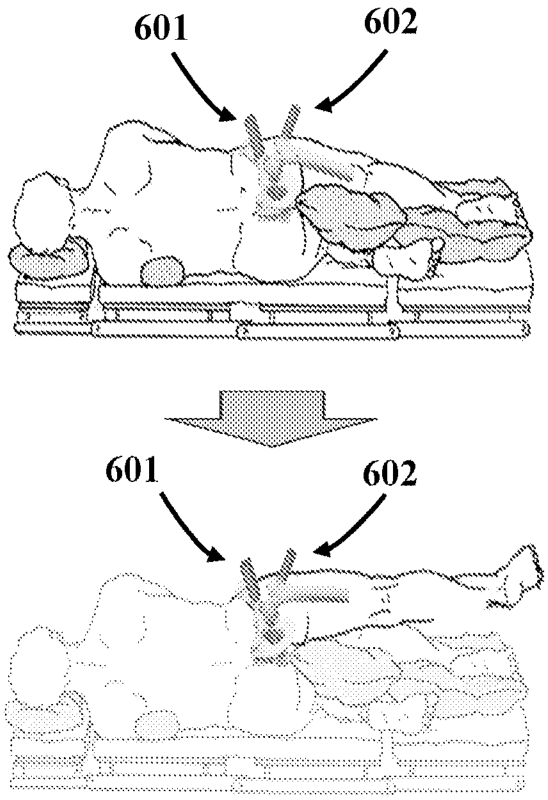
Figure 14A:
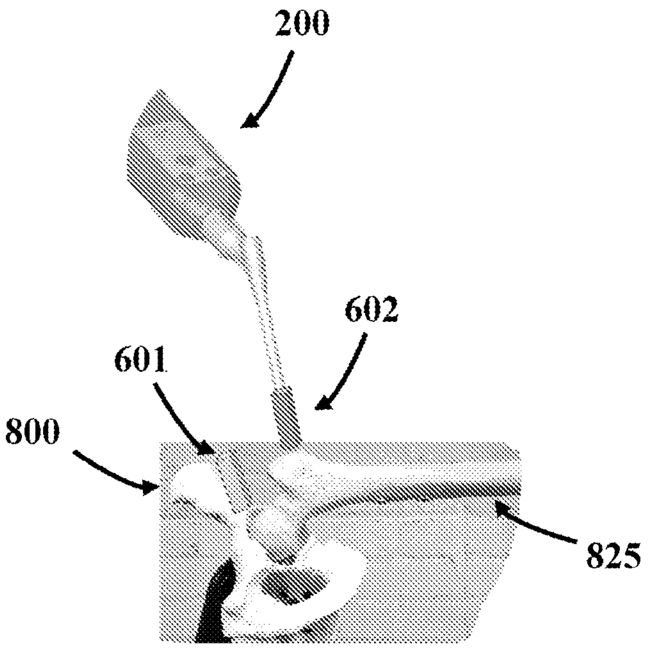
FIGS. 14A and 14B further illustrate components of a surgical navigation system during an operating step, according to embodiments of the invention. In particular.
Figure 14B:
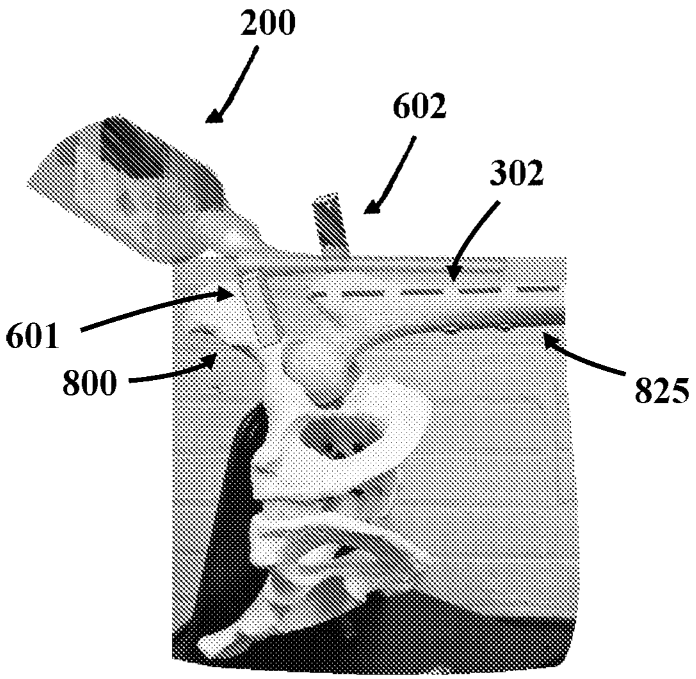

In some embodiments, once both first marker 601 and second marker 602 are placed, the patient may be repositioned such that a neutral position of the leg is achieved (i.e., neutral flexion/extension, adduction/abduction, and internal/external rotation) (see FIG. 13B).

Figure 15:
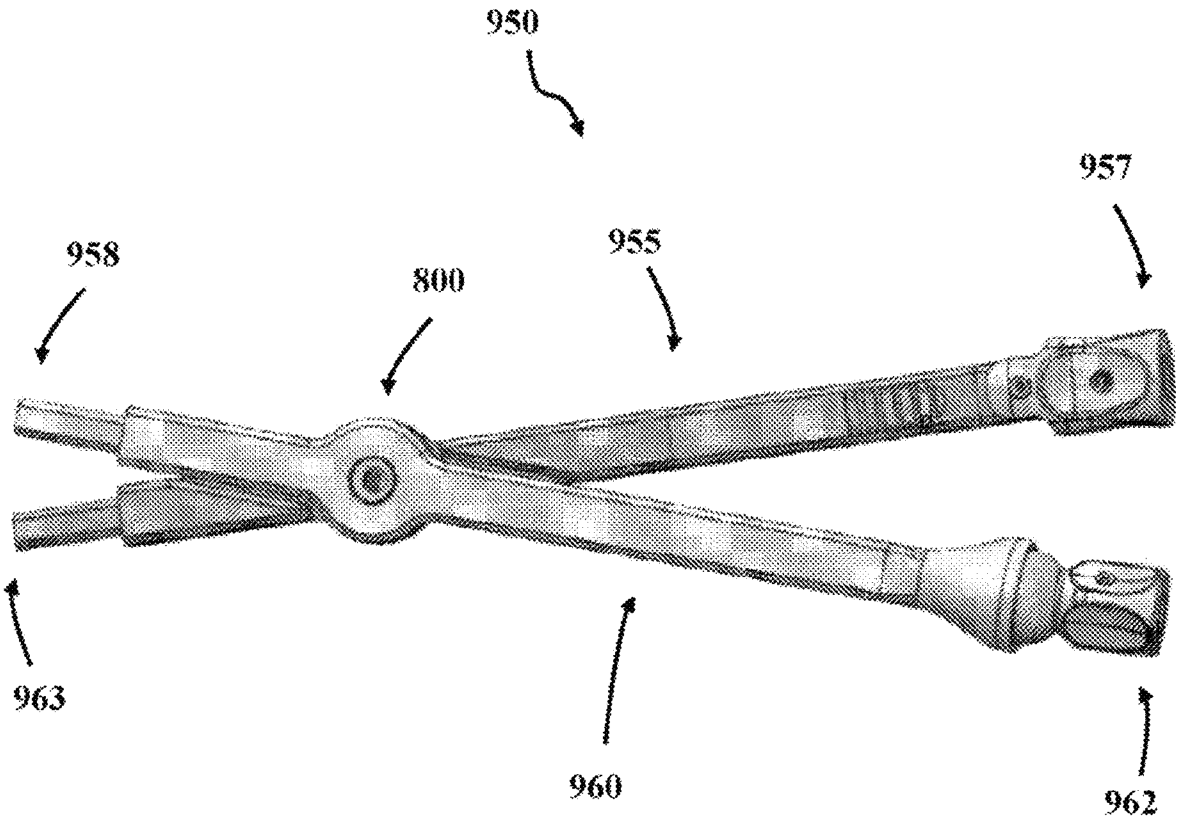
FIG. 15 illustrates the linear measurement device (LMD) according to embodiments of the invention.

In some embodiments, the handheld surgical tool may be used to measure the initial leg position. In certain embodiments, a tool may be used for the initial linear measurements, for example, a Linear Measurement Device (LMD) as shown in FIG. 15. The LMD 950 comprises a first arm 955 having a proximal end 957 and a distal end 958, and a second arm 960 having a proximal end 962 and a distal end 963. The first arm 955 and the second arm 960 are connected by a joint 965 that allows the first arm 955 and the second arm 960 to rotate relative to each other. The proximal end 957 of the first arm 955 and the proximal end 962 of the second arm 960 are each configured to engage with a marker. The distal end 958 of the first arm 955 and the distal end 963 of the second arm 960 are configured to engage with a marker engager 610 attached to the handheld surgical tool 200. During use, the LMD 950 is engaged with both the pelvic marker 60 land the femoral marker 602. The handheld surgical tool 200 is engaged with the first arm 955 of the LMD 950 and recorded, and the handheld surgical tool 200 is then engaged with the second arm 960 of the LMD 900 and recorded. In the software, a vector representing each of the arms 955, 960 of the LMD 900 is constructed in patient coordinates from the recorded quaternion of the handheld surgical tool 200. The second vector recorded is subtracted from the first vector recorded. This vector represents the distance between the two markers, pointing from the pelvic marker 601 to the femoral marker 602.

As illustrated in FIG. 16, imaging device 500 images the relevant patient anatomy, including the first marker 601 and the second marker 602. For example, the imaging device 500 may be a three-dimensional scanning tool that captures data corresponding to the shape/surface of the pelvis and the location and orientation of the markers 601 and 602. A processor generates a three-dimensional surface/model 700 of the pelvis and the markers 601 and 602 from the imaging data. Bone features, such as the shape of the acetabulum (coronal and sagittal plane), as well as the markers and their orientation in relation to patient anatomy, can be detected based upon three-dimensional surface/model 700. Additionally, the processor can calculate relevant orientations and distances, such as intra-operative leg length (ILL), leg length discrepancy (LLD), and offset for the patient prior to (and after) the hip replacement procedure because the system has positional information of marker 601 and 602, in a neutral position relative to one another and relative to horizontal vector 301. This allows for the system to determine a proper angle and a suitable starting location on the femur's neck for cutting of the femur's head. Moreover, by imaging in the neutral position, an accurate leg length can be calculated.

Figure 17:
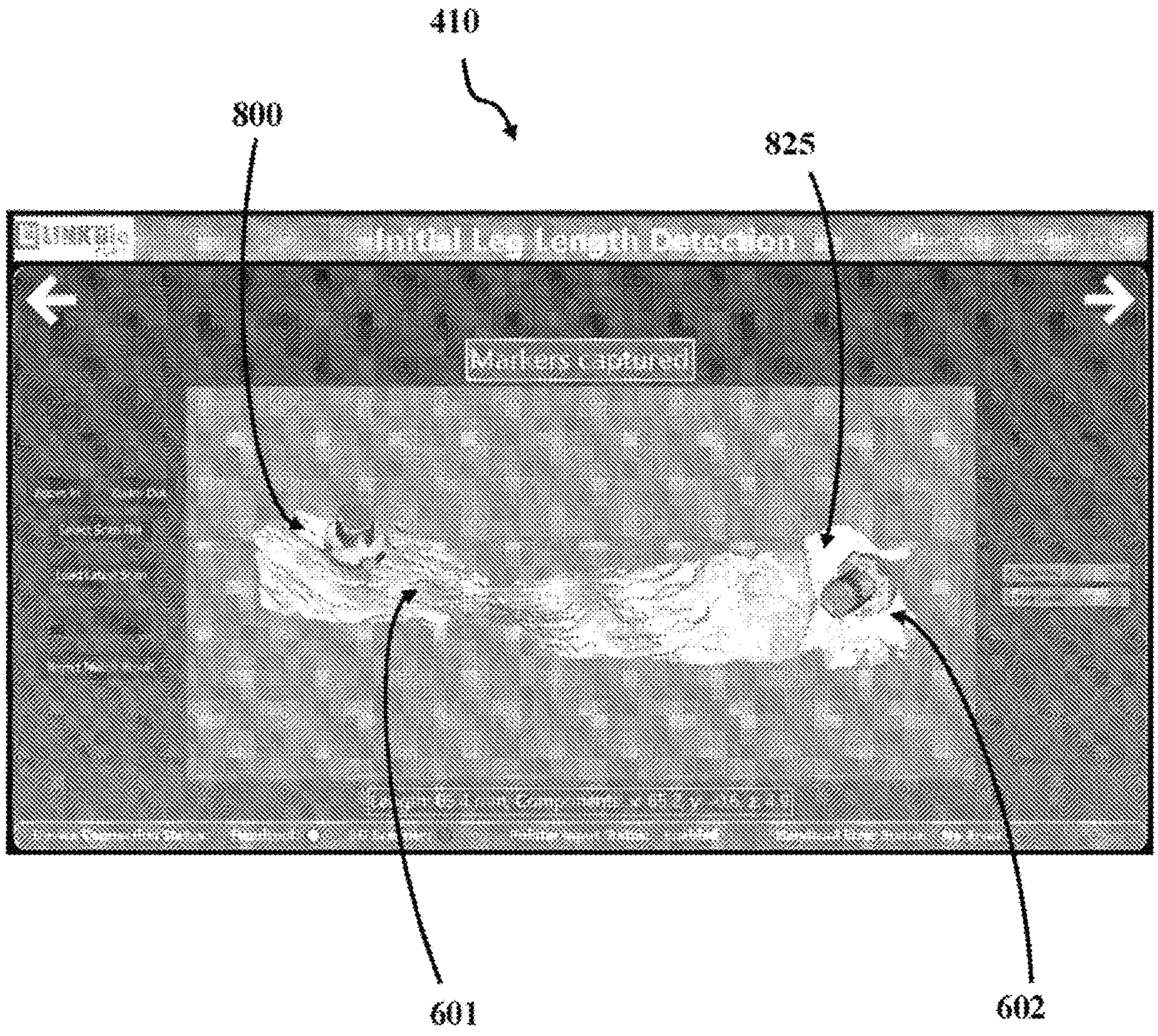
FIG. 17 illustrates an example of an initial leg offset scan with markers detected shown on a visual display according to embodiments of the invention.

In some embodiments, the three-dimensional scanning tool is used to obtain a single point cloud file in which both the pelvic and femoral markers are visible (see FIG. 17). The process may run a point cloud matching algorithm on the three-dimensional scan to identify the location and orientation of each marker in scan coordinates. Pre-scanned point clouds of the individual markers with a known orientation may be provided to the algorithm as source data for matching. The point cloud matching algorithm can use random sample consensus to find an approximate transformation (i.e., location and orientation) for the first marker 601 and second marker 602 in the target scan. The approximate transformation is then refined to an exact transformation by an iterative closest point calculation.

In embodiments in which the pelvic marker orientation has been recorded, the quaternion rotation between scan axes and patient axes can be calculated. First, the quaternion rotation $q_{engagement\ correction}$ from the pelvic marker engagement axis in scan coordinates to the engagement axis in patient coordinates is calculated. Then, the roll is accounted for by finding $q_{roll\ correction}$ as the quaternion rotation from the roll vector in scan coordinates rotated by $q_{engagement\ correction}$ to the roll vector in patient coordinates. The overall scan-to-patient coordinate quaternion is then: $q_{scan\ to\ patient}=q_{roll\ correction}*q_{engagement\ correction}$. The vector connecting the centers of the two markers is then calculated and recorded in patient coordinates by rotating the same vector in scan coordinates by $q_{scan\ to\ patient}$ as follows: $v_{intermarker,patient}=q_{scan\ to\ patient}*v_{intermarker,scan}*q_{scan\ to\ patient}^{-1}$. The pelvic and femoral marker orientation vectors are similarly converted to patient coordinates.

In some embodiments, a rigid guide connecting both markers may be placed in the wound to simplify the process of obtaining a scan of both markers. This guide may allow the three-dimensional scanner to follow a fixed path from one marker to the other, thus avoiding the technical difficulty of scanning a path across mobile soft tissues.

In some embodiments, a mark 603 (e.g., divot, bur, or bowie) may be further placed on the femoral head, as illustrated by FIG. 16. The imaging unit images the surgical area again in order to capture markers 601 and 602 and mark 603. As further illustrated by FIG. 16, femoral axis 302 may be displayed on the subsequently generated three-dimensional surface/contour 700.

With this positional information the visual display 410 can indicate where a cutting jig is to be placed such that it properly aligns with femoral axis 302 so that the femoral head is properly resected (i.e., cut at the proper angle).

Figure 18:
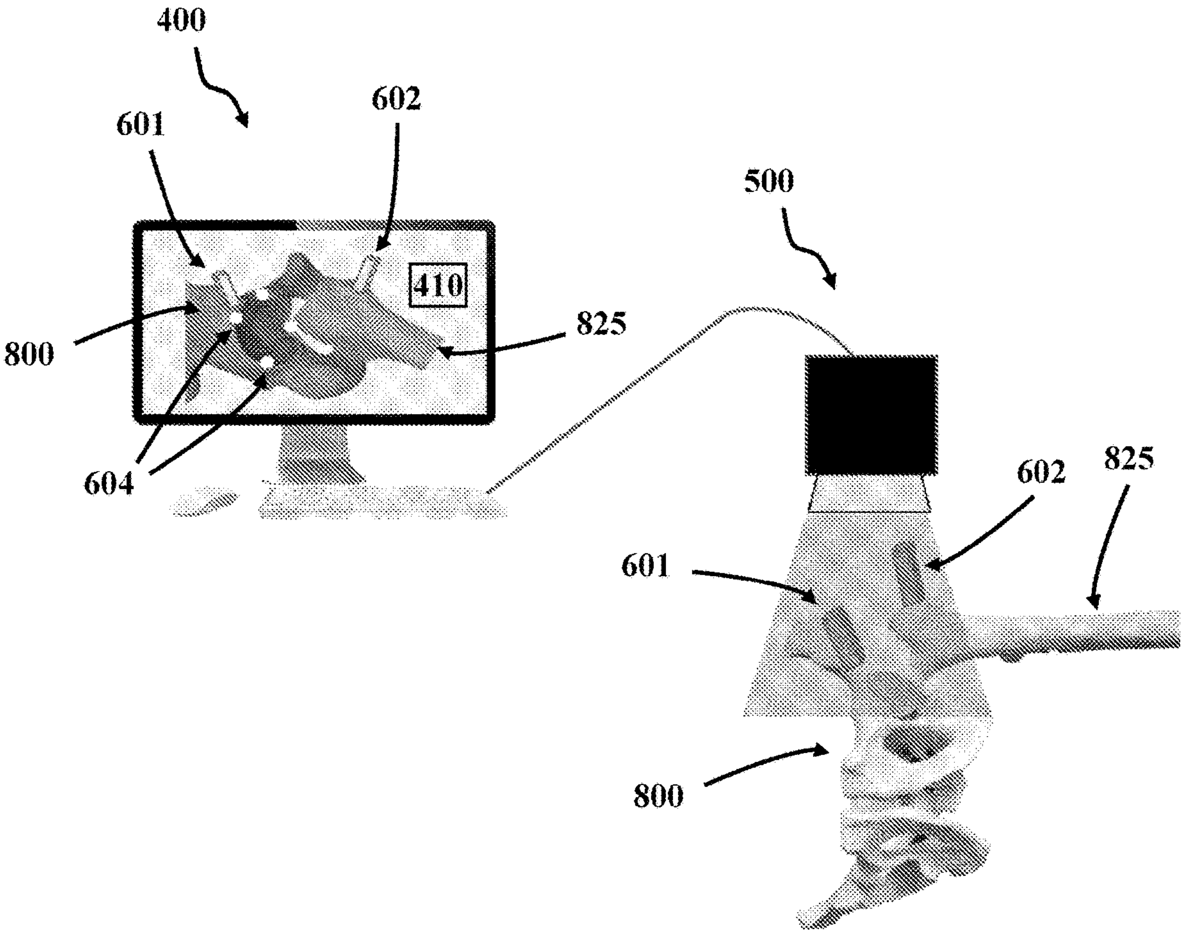
FIG. 18 illustrates components of a surgical navigation system during a further operating step according to embodiments of the invention, in which the imaging device images the relevant anatomy after resection and a plurality of points on the acetabulum are located.

In some embodiments, imaging device 500 images the relevant anatomy, after resection, in order to generate relevant anatomical features, such as features of the acetabulum. According to embodiments, three-dimensional surface/contour 700 is generated from the image data and analyzed in order to locate a plurality of points 604 on the acetabulum, as illustrated by FIG. 18. These points, according to one preferred embodiment, correspond to the acetabular notch and the top, left, and right acetabular rim. With this information the system determines the coronal plane, which may be displayed on visual display 410 in conjunction with the three-dimensional surface/contour 700.

Figure 19A:
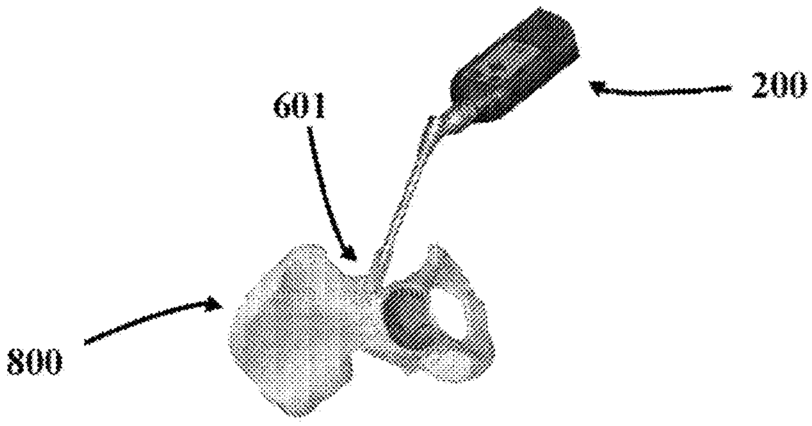
FIGS. 19A-19C illustrate component of a surgical navigation system during a further operating step according to embodiments of the invention.

A set of steps may be carried out to effectuate a computer aided surgical procedure. The handheld surgical tool 200 may be placed in real space at the starting point, such as within/on marker 601 (e.g., via a marker engager 610), as illustrated by FIG. 19, in order to establish a starting reference point for the procedure.

Figure 20:
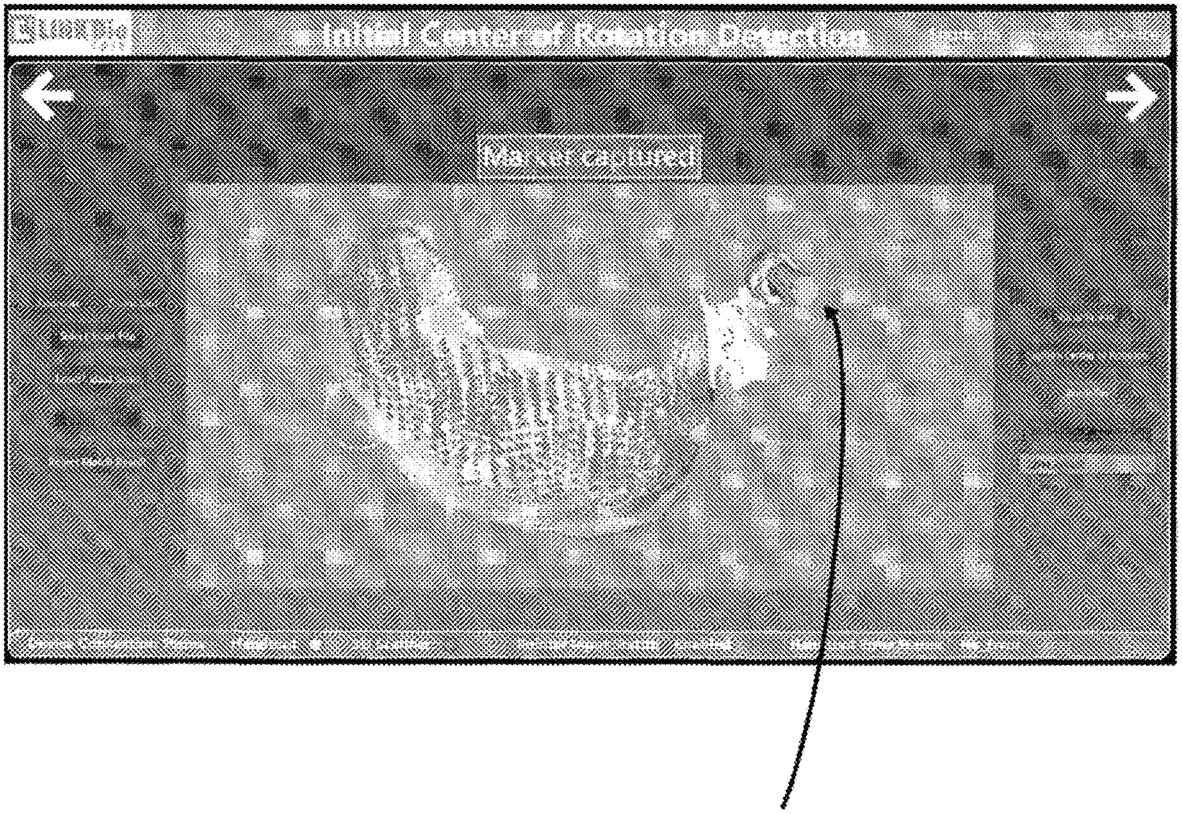
FIG. 20 illustrates an example of brush selection of points on the lunate surface of the acetabulum for center of rotation detection shown on a visual display according to embodiments of the invention.
Figure 21:
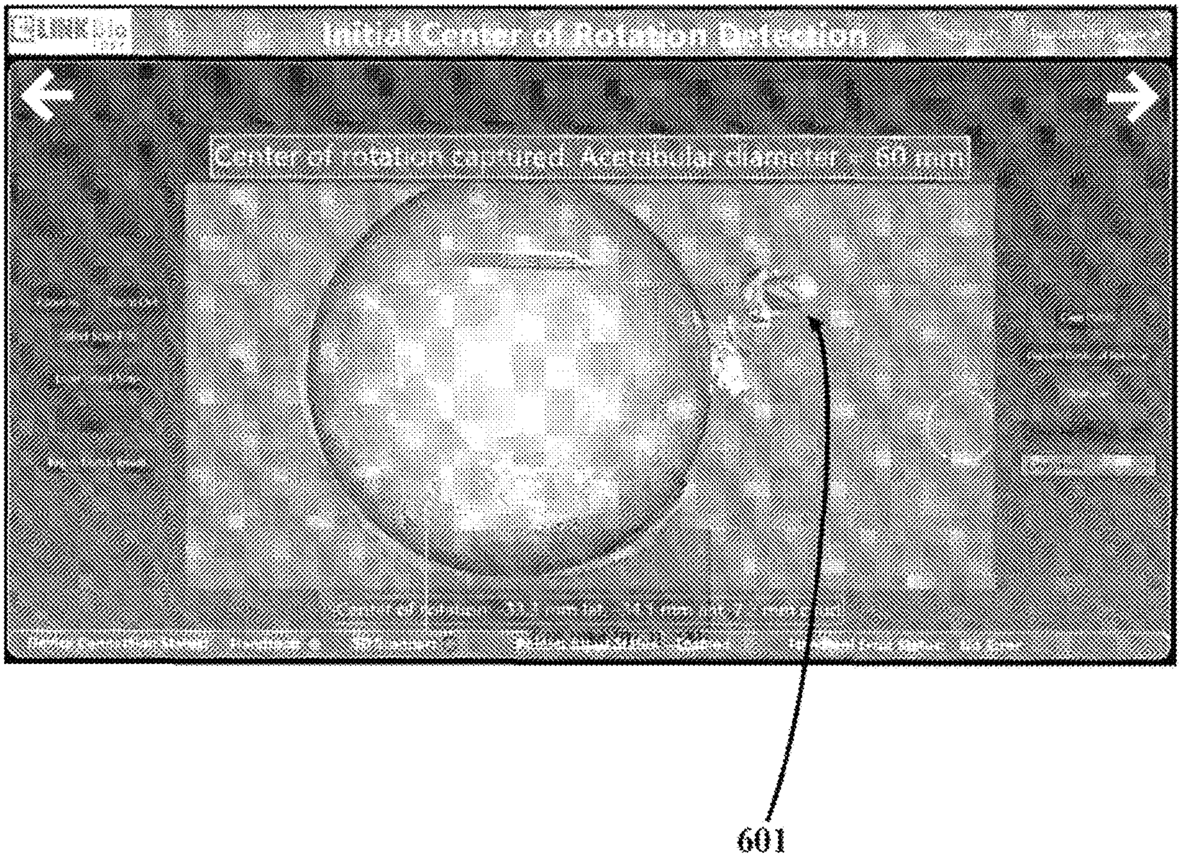
FIG. 21 illustrates an example of detected center of rotation and acetabular diameter shown on a visual display according to embodiments of the invention.

In certain embodiments, the imaging device 500 obtains a single point cloud file in which the pelvic marker and the lunate surface of the acetabulum are visible. A point cloud matching algorithm may be run on the imaging data to identify the location and orientation of the pelvic marker in scan coordinates, and the orientation is then adjusted to patient coordinates. In certain embodiments, in the UI, a brush selector tool 505 (see FIG. 20) may be used to select points on the lunate surface of the acetabulum, and a sphere is fit to those points using a least squares calculation. The center of the best fit sphere in patient coordinates, relative to the center of the pelvic marker, gives the native center of rotation of the hip (see FIG. 21). The diameter of the sphere could be used to suggest a cup size and reaming sequence to the surgeon.

In some embodiments, before beginning the cup orientation targeting, or at any other time desired after recording the pelvic marker orientation vectors in patient coordinates, the handheld surgical device may be tared to re-establish the handheld surgical device-to-patient adjustment quaternion, because the axes of the handheld device may drift over time or the pelvis could move on the operating table. The handheld device can be engaged with the pelvic marker in a unique orientation, and orientation is recorded (for example, by pressing the set key). The handheld-device-to-patient adjustment quaternion may be recalculated by finding the quaternion rotation from the marker engagement axes in handheld device coordinates to the marker engagement axes in patient coordinates (recorded as described herein).

Figure 19B:
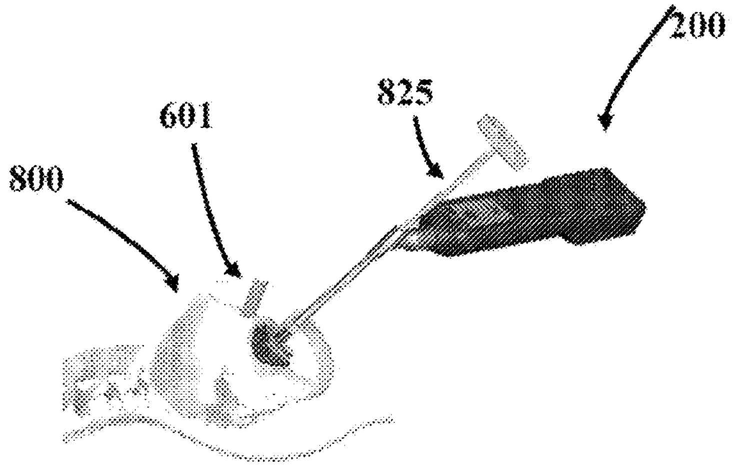
Figure 19C:
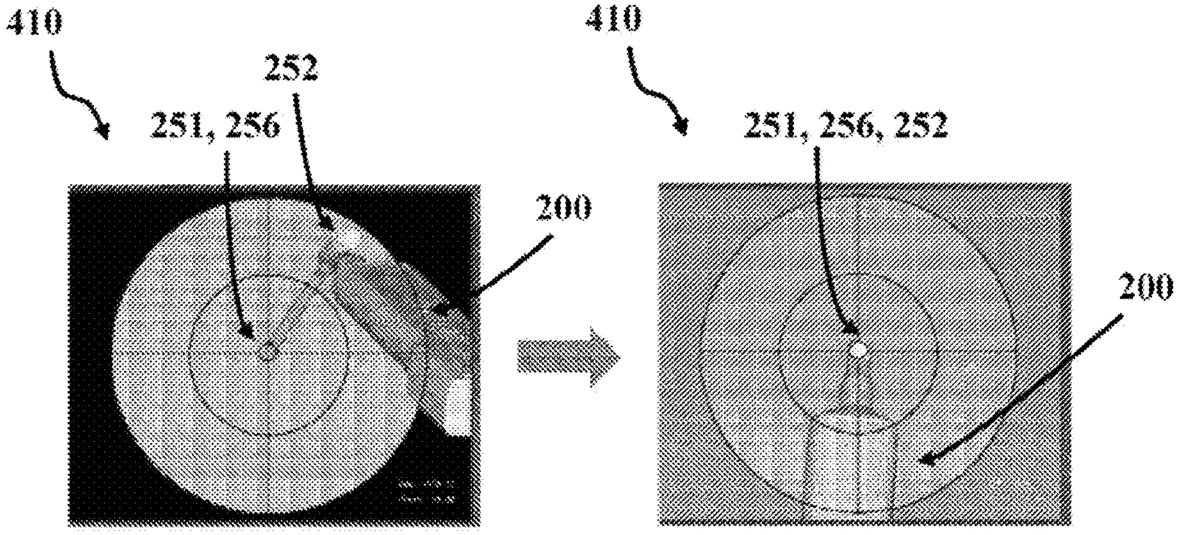
Figure 22:
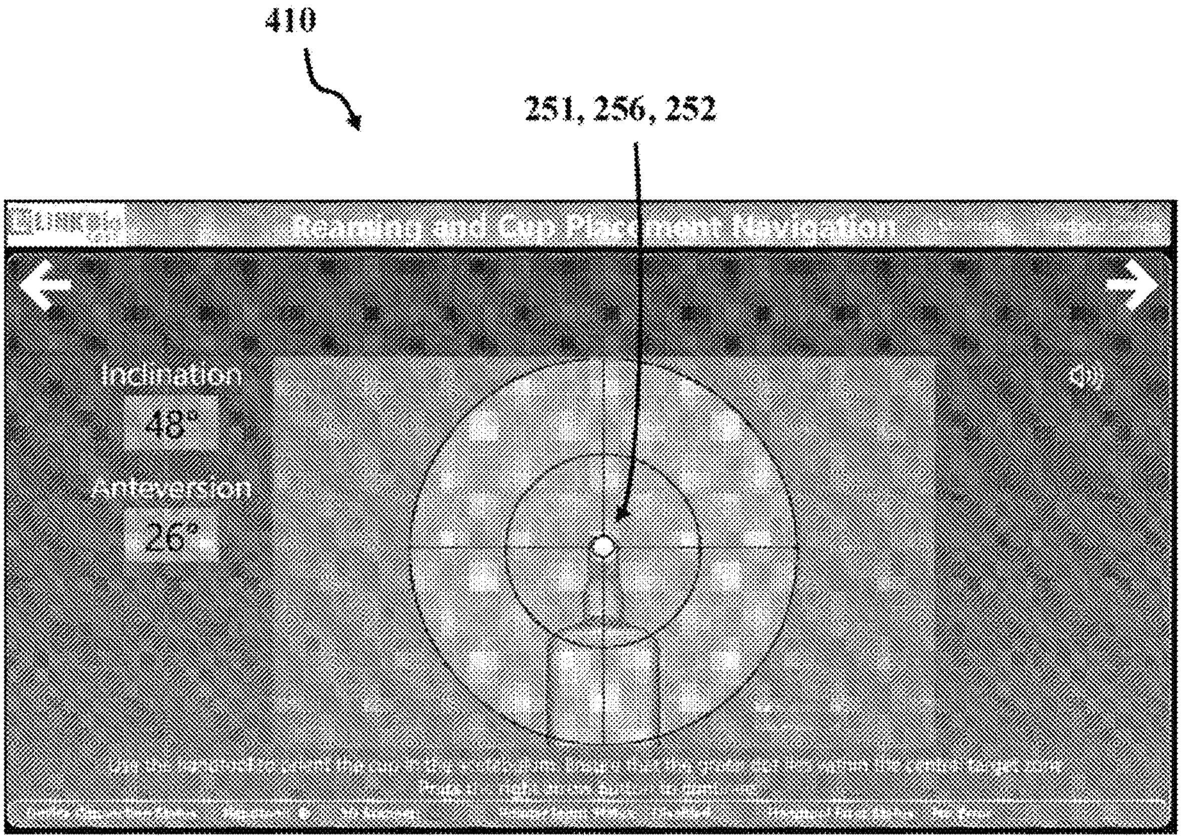
FIG. 22 illustrates an example of a targeting interface for reaming and cup orientation navigation shown on a visual display according to embodiments of the invention.

According to some embodiments, the shaft of the handheld surgical tool may then be fitted with the instrument shaft of a reaming tool or cup impactor 850 such that the reaming tool or cup impactor is located within the acetabulum (see FIG. 19B. When the handheld device is engaged, the software will guide the surgeon to hold the cup impactor or reamer in the desired orientation by means of a bullseye targeting interface (see FIGS. 19C and 22). Once the acetabulum is properly reamed, a prosthetic cup is implanted therein.

Figure 23:
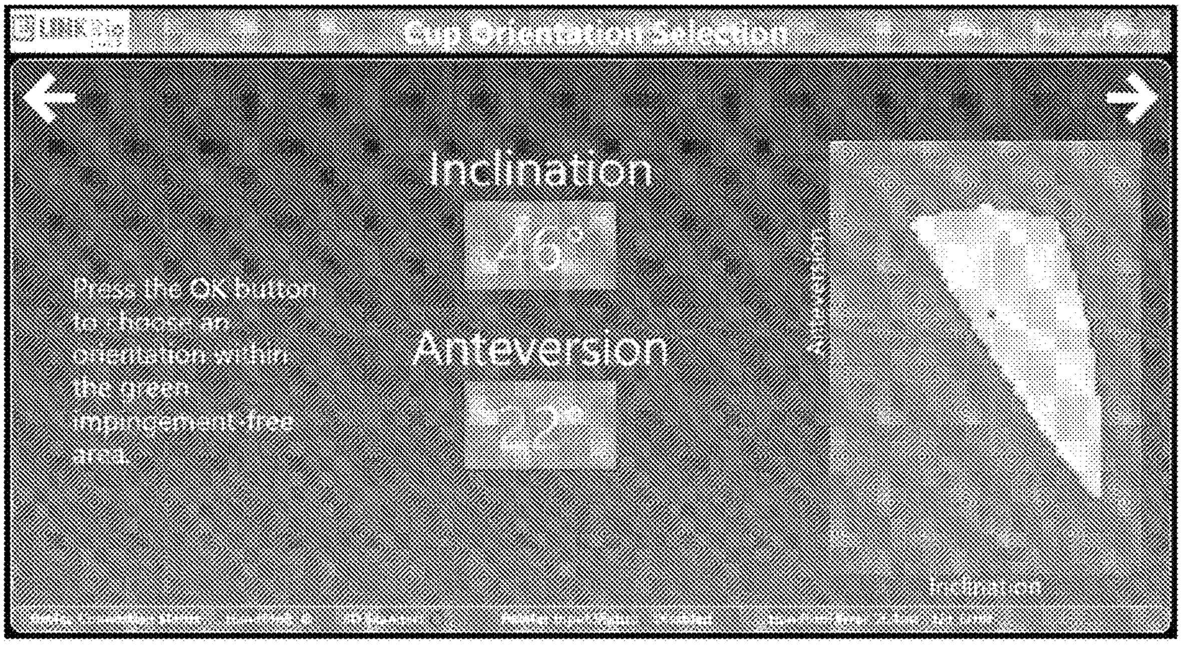
FIG. 23 illustrates selection of cup orientation angles from range of motion model output graph shown on a visual display according to embodiments of the invention.

In some embodiments, after the cup is placed in the acetabulum, the surgeon can adjust the orientation of the cup according to feedback from the software as to its location within the impingement-free zone defined by the range of motion model (see FIG. 23). The surgeon can choose a desired orientation, integrating feedback from the range of motion model with the patient's specific anatomy.

In some embodiments, after the cup is impacted, a liner is placed into the cup. In certain embodiments, an appropriately sized trial head is placed into the liner before scanning, to facilitate detection of the new center of rotation by a point cloud matching algorithm. In certain embodiments, the center of rotation is detected by scanning the empty liner and fitting a sphere to points selected on the spherical surface of the liner.

Figure 24:
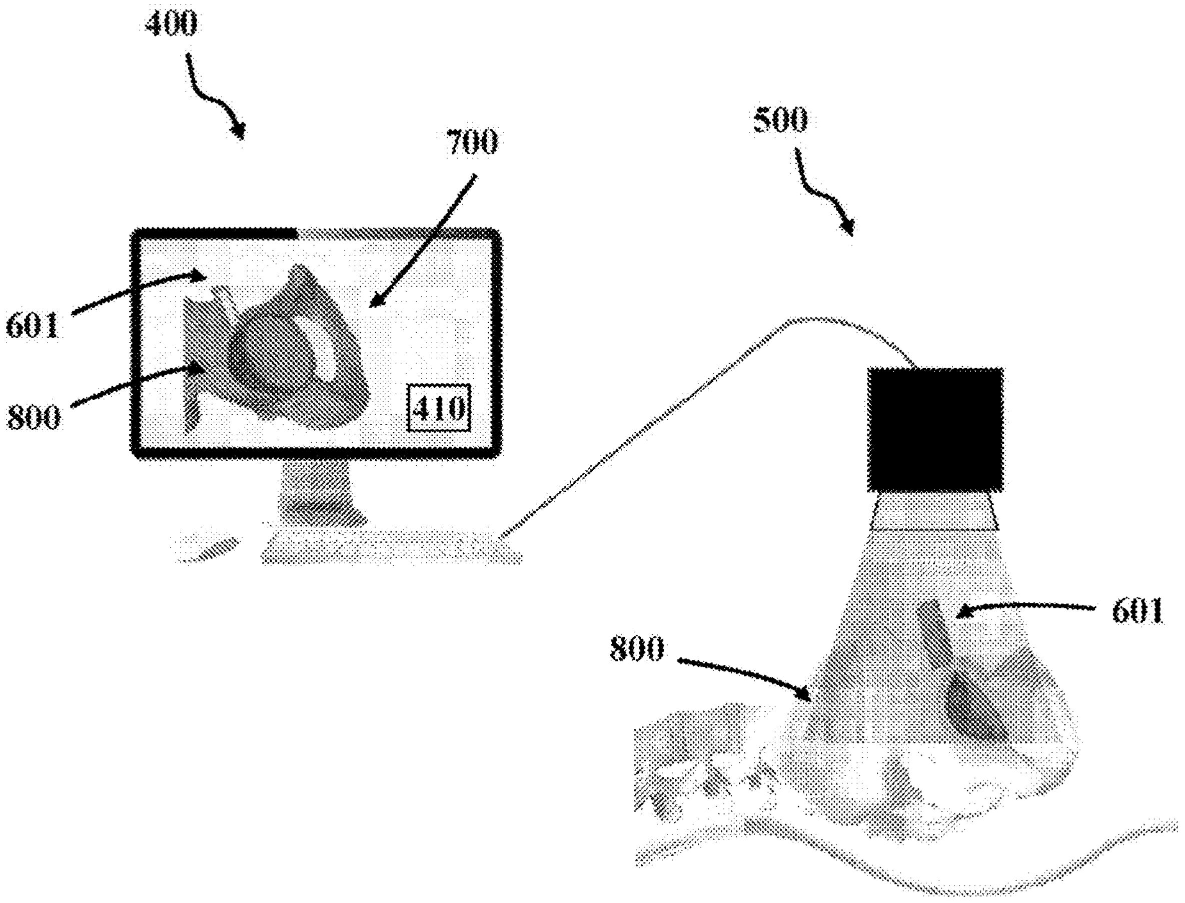
FIG. 24 illustrates components of a surgical navigation system during a further operating step according to embodiments of the invention, in which a new three-dimensional contour/surface is generated from additional scanning.

As FIG. 24 depicts, a new three-dimensional contour/surface 700 may be generated, which is based upon image data generated by imaging device 500 of the acetabulum, and which includes first marker 601 and the implanted cup. An updated acetabular plane may then be calculated and may be displayed in relation to the three-dimensional contour/surface 700. Anteversion and inclination of the implanted cup can also be calculated from the three-dimensional contour/surface 700.

Figure 25:
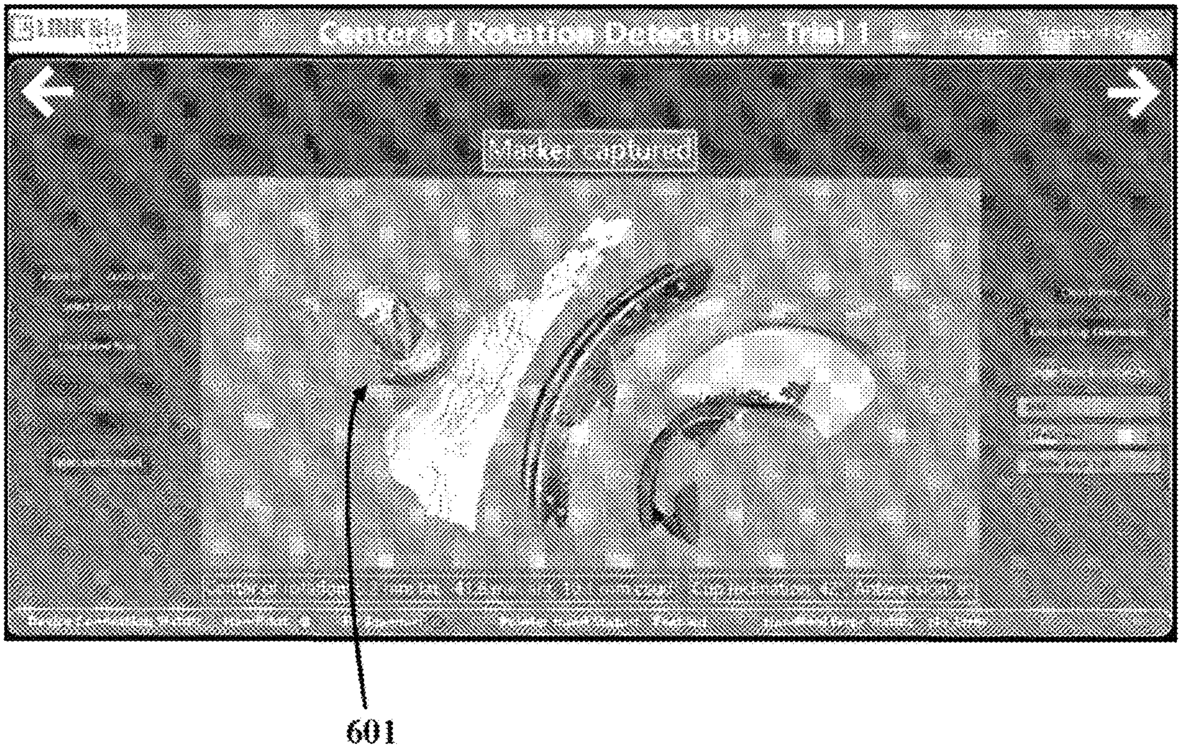
FIG. 25 illustrates trial center of rotation scan, displaying detected marker, detected trial head and center of rotation, selected points on the rim of the implanted cup, and detected cup orientation, and shown on a visual display according to embodiments of the invention.

In some embodiments, the imaging device 500 may obtain a single point cloud file in which the pelvic marker, the rim of the implanted cup, and trial head are visible (see FIG. 25). A point cloud matching algorithm can be run on the three-dimensional scan to identify the location and orientation of the pelvic marker in scan coordinates, and the location of the center of rotation relative to the pelvic marker. These values are converted to patient coordinates. In certain embodiments, several points are chosen along the rim of the implanted acetabular cup, and the radiographic inclination and anteversion angles of the cup are calculated from the normal vector to the best-fit plane of those chosen points (i.e. the cup axis, $\vec{a}_{cup}$). The cup axis is then projected onto the coronal plane (coronal normal vector $\vec{n}_{coronal}=\hat{J}$) by the following formula:

$$\vec{a}_{cup,coronal} = \vec{a}_{cup} - \frac{\vec{a}_{cup}\cdot\hat{J}}{\|\vec{a}_{cup}\|^2}\vec{a}_{cup}.$$

The inclination is calculated as the angle between $\vec{a}_{cup,coronal}$ and the longitudinal axis of the patient ($\hat{k}$):

$$\text{inclination } [deg] = \frac{180}{\pi}\cos^{-1}\left(\frac{\vec{a}_{cup,coronal}\cdot\hat{k}}{\|\vec{a}_{cup,coronal}\|\|\hat{k}\|}\right).$$

The anteversion is calculated as the angle between the cup axis and its projection on the coronal plane:

$$\text{anteversion } [deg] = \frac{180}{\pi}\cos^{-1}\left(\frac{\vec{a}_{cup,coronal}\cdot\vec{a}_{cup}}{\|\vec{a}_{cup,coronal}\|\|\vec{a}_{cup}\|}\right).$$

In other embodiments, the radiographic inclination and anteversion angles of the cup axis are calculated by matching a three-dimensional model of the cup rim with known orientation to the three-dimensional scan, using a point cloud matching algorithm.

In some embodiments, the femur may be broached prior to acetabular cup placement. In alternative embodiments, the femur may be broached after acetabular cup placement.

Once the cup has been implanted and the femur has been resected, a trial stem may be placed into the femur. Based upon the imaging data and determined orientations/angles/distances, the system can calculate optimal prosthetic components, such as optimal stem, head, insert, and adaptor. Imaging device 500 can image the relevant anatomy when the trial is implanted to test conformity of the prosthetic.

In some embodiments, the imaging device 500 is used to obtain a single point cloud file including both the femoral and pelvic markers. A point cloud matching algorithm may be run on the three-dimensional scan to identify the location and orientation of each marker in scan coordinates. Because the pelvic marker orientation is known in patient coordinates, the quaternion rotation between scan axes and patient axes can be calculated. The orientation vectors of the markers and the vector connecting the centers of the two markers are calculated and recorded in patient coordinates.

Once the final prosthetic is implanted another imaging device 500 can image the relevant anatomy again to measure the Leg Length Discrepancy (LLD) and Offset and fine-tune the choice of implant's elements to reduce LLD and offset to zero (or to a predefined value).

In some embodiments, the length offset change may be calculated. The change in leg offset for the current trial with respect to the native offset is reported in the mediolateral (x), anteroposterior (y), and craniocaudal (z) directions in the surgical summary display. In order to reliably compare the data between the initial and trial inter-marker scans, the trial leg may be virtually rotated around the trial center of rotation to match the leg orientation in the initial scan, before finding the offset change as the difference between the trial and initial inter-marker distances. The leg orientation is defined by the femoral marker orientation. To find the transformation from the trial leg orientation to the initial leg orientation ($T_{1\rightarrow 0}$), the matrix system is solved:

$$T_{1\rightarrow 0} = \begin{bmatrix} a_{0_x} & b_{0_x} & c_{0_x} \\ a_{0_y} & b_{0_y} & c_{0_x} \\ a_{0_z} & b_{0_z} & c_{0_x} \end{bmatrix}\left(\begin{bmatrix} a_{1_x} & b_{1_x} & c_{1_x} \\ a_{1_y} & b_{1_y} & c_{1_x} \\ a_{1_z} & b_{1_z} & c_{1_x} \end{bmatrix}\right)^{-1}$$

Where $\vec{a}_0$ is the initial femoral marker axis in patient coordinates, $\vec{b}_0$ is the initial femoral marker roll vector in patient coordinates, and $\vec{c}_0=\vec{a}_0\times\vec{b}_0$; $\vec{a}_1$ is the trial femoral marker axis in patient coordinates, $\vec{b}_1$ is the trial femoral marker roll vector in patient coordinates, and $\vec{c}_1=\vec{a}_1\times\vec{b}_1$. If $m_{f_1}(x, y, z)$ is defined as the center of the femoral marker in patient coordinates as measured in the trial scan, and $c_1(x, y, z)$ as the trial center of rotation in patient coordinates, then $\vec{v}_1=m_{f_1}-c_1$ is the vector pointing from the trial center of rotation to the center of the femoral marker as measured in the trial scan. To adjust the location of the femoral marker in the trial scan according to the orientation of the leg in the initial scan, $m_{f_{1,adj}}=T_{1\rightarrow 0}\vec{v}_1+c_1$ is calculated. The change in offset is: $\Delta\text{offset}=m_{f_{1,adj}}-m_{f_0}$.

In some embodiments, a "Position Planning" program may be initiated at the beginning of the surgery. The Position Planning program requires input by the user of one or more of the following: (i) confirmation or changes to the surgical workflow options; (ii) the cup position-planning model; (iii) implants expected to be used in the surgery, in which their geometric parameters are automatically inputted into the chosen cup position model; and (iv) patient's sitting and standing pelvic tilts. In some embodiments in which the acetabulum is prepared before the femur, the patient's native femoral antetorsion may be inputted to the model, and the implant antetorsion is calculated as the sum of the native antetorsion and the designed antetorsion of the chosen stem. In other embodiments in which the femur is prepared before the acetabulum, the patient's native femoral antetorsion may not be inputted to the model, and the implant antetorsion is measured by engaging the handheld surgical tool with the implanted stem. The engagement vector may be recorded in patient coordinates, and the known transformation between the engagement axis and the stem axis may be used to calculate the stem orientation in patient coordinates.

In some embodiments, the LMD may also be used to measure LLD or offset, but to do so, the two markers need to have the same relative orientation before and after in order to make the distance measurements comparable. This can be achieved by defining a neutral position, e.g., to reproduce the patient in a standing position by holding the leg up (lateral decubitus) or by placing the leg parallel to the other one (supine); or alternatively, by using the LMD to navigate accurately the femur orientation. By recording the orientation of the femoral marker before the implantation of the prosthesis, the marker engager attached to the handheld surgical tool can engage the femoral marker again, and then the femur can be moved until the femoral marker achieves the same orientation as prior to the implantation.

In certain embodiments, there is an option to save a patient's position plan, including selection of cup placement model, surgical implant parameters, and patient specific geometric parameters, to a local database. In addition, a randomly generated surgery ID may be assigned to each saved position plan. The position plan will not contain patient-identifying information.

In certain embodiments, a position plan may be selected from a list of saved position plans, and either load the data into the GUI module, or transfer the data to another computer.

Shoulder Arthroplasty

In embodiments of the invention, the surgical navigation system of the present invention may be used for performing shoulder arthroplasty including, but not limited to, anatomical shoulder arthroplasty, reverse shoulder arthroplasty, tumor shoulder arthroplasty, and revision shoulder arthroplasty. In particular, the surgical navigation system of the present invention may be used to determine correct implant positioning.

In some embodiments, use of the surgical navigation system for shoulder arthroplasty involves registering the position of the glenoid with the handheld surgical tool and mapping it to a three-dimensional model. This three-dimensional model is generated from a computerized tomography (CT) scan or a magnetic resonance image (MRI).

In embodiments of the invention, a pre-planning data file may be generated for use with the shoulder arthroplasty. The pre-planning data file may contain information including, but not limited to: (i) the three-dimensional geometry of the patient's operative scapula derived from a CT or MRI scan; (ii) whether the operative scapula is a right or a left scapula; (iii) a three-dimensional point representing a planned K-Wire entry point in the coordinate system of the three-dimensional model; (iv) a three-dimensional vector representing a planned K-Wire direction in the coordinate system of the three-dimensional model from the planned entry point; (v) a three-dimensional point representing the most superior point on the glenoid in the coordinate system of the three-dimensional model; (vi) a three-dimensional point representing the most inferior point on the glenoid in the coordinate system of the three-dimensional model; (vii) a three-dimensional point representing the most posterior point on the glenoid in the coordinate system of the three-dimensional model; (viii) a three-dimensional point representing the most anterior point on the glenoid in the coordinate system of the three-dimensional model; and/or (ix) a three-dimensional point representing the center point of the glenoid in the coordinate system of the three-dimensional model. In some embodiments, the anterior, posterior, superior, inferior, and center points of the glenoid shall be chosen algorithmically.

Prior to the surgery, the pre-planning data file shall be imported into the GUI module for annotation of the patient's three-dimensional scapula model. During the annotation process, information extracted from the three-dimensional model may be used to register the intraoperative orientation of the patient's glenoid, and thereby map the pre-planned k-wire orientation onto the patient's real glenoid.

In some embodiments, the scapular model shall be displayed in the GUI module, along with the points described as being in the pre-planning data file. The user may have the opportunity to confirm or re-do the selection of these points, but not the k-wire direction and entry point.

To set up for surgery, the handheld surgical tool is initialized, i.e., it measures the direction of gravity and orients its axes such that its Y-axis points opposite to gravity. The operative shoulder may then be exposed, and soft tissues are removed that are not visible on the three-dimensional model. The K-Wire insertion position may be marked on the glenoid using electrocautery.

In some embodiments, a marker may be installed on the scapula. The marker may be able to engage with the handheld surgical tool in a manner according to embodiments of the invention, to allow the orientation of the marker to be recorded.

In some embodiments, the glenoid may be scanned using the 3D scanner, such that physical attributes of the glenoid may be identified instead of markers.

On the visual display, a three-dimensional model of the patient's glenoid may be displayed.

After the transformation between the handheld surgical tool and glenoid coordinate, the GUI module can display a three-dimensional animation depicting the real-time computed orientation of the handheld surgical tool with attached tool in relation to the patient's glenoid. As the user moves the tool, the user can confirm that the orientation and motion of the tool relative to the patient's glenoid scan in the three-dimensional animation matches the orientation and motion of the tool relative to the patient's actual glenoid on the operating table.

In some embodiments, the transformation between the handheld surgical tool and glenoid coordinate system may be computed by means of a contour tracing. In such embodiments, a jig that interfaces with the handheld surgical tool may be installed on the glenoid. The handheld surgical tool can be traced along the surface of the glenoid, and the transformation shall be calculated by matching the recorded contour to the expected one.

In some embodiments, the orientation of a marker installed on the scapula can be recorded by engaging with the handheld surgical tool. Subsequent re-engagement with the scapula marker can allow for a recalculation of the transformation between the handheld surgical tool and the glenoid coordinate systems, thereby eliminating accumulated errors including, but not limited to, errors due to gyroscope drift, and mobility of the patient's scapula.

In some embodiments, distances in the shoulder may be measured with a scanner or LMD as described for the hip arthroplasty. Similarly, center of rotation may be measured for the shoulder as described for the hip arthroplasty.

Figure 26:
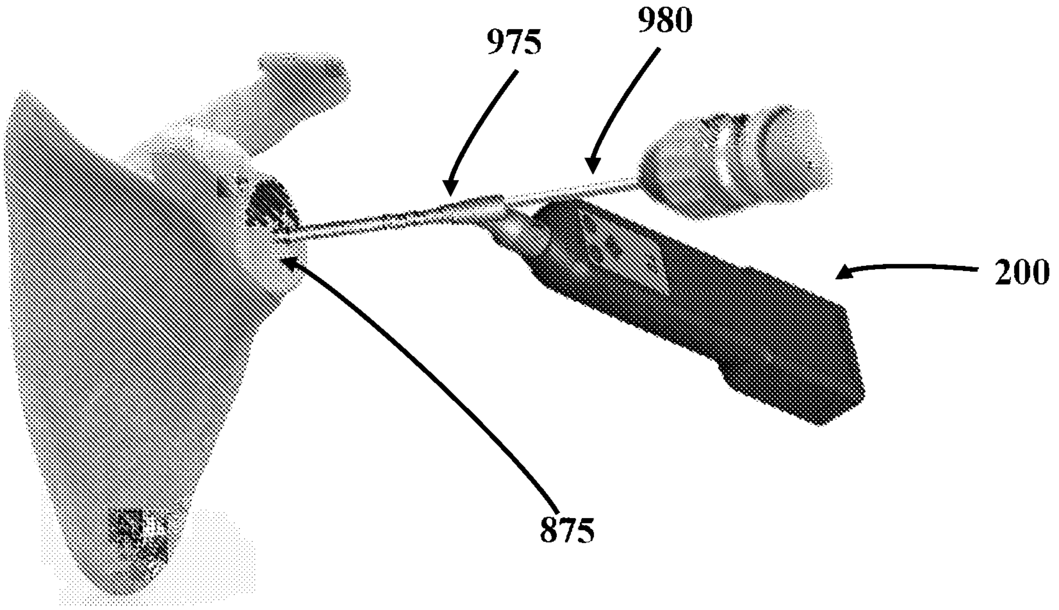
FIG. 26 illustrates a demonstration of the K-Wire being drilled into the glenoid while being guided by the handheld surgical tool and attached K-Wire guide.
Figure 27A:
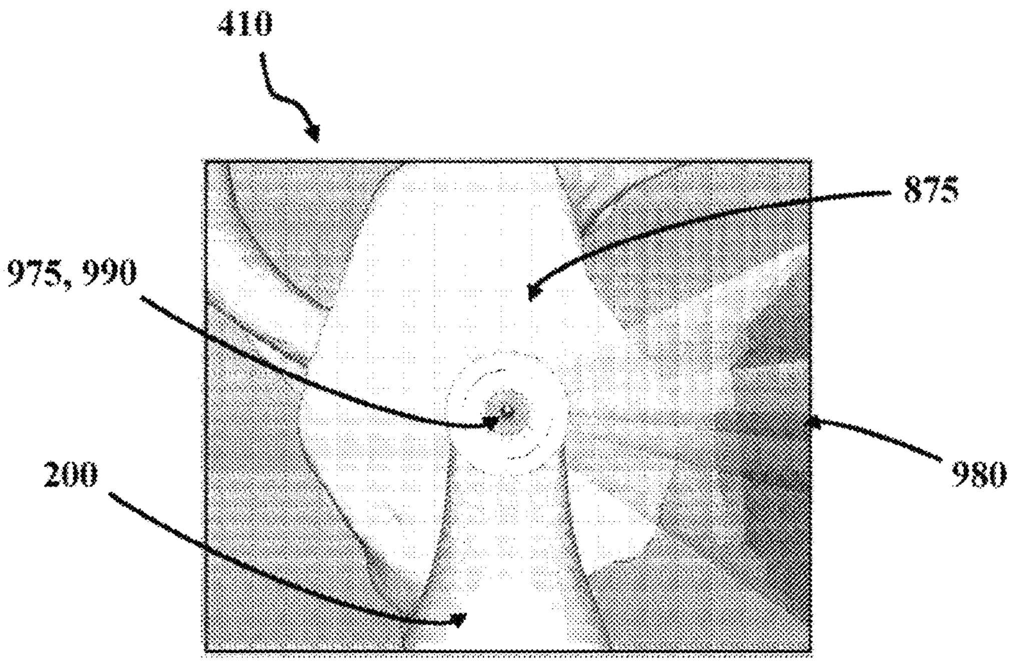
FIGS. 27A and 27B illustrate an example of the K-Wire trajectory guidance interface provided by the surgical navigation system according to embodiments of the invention.
Figure 27B:
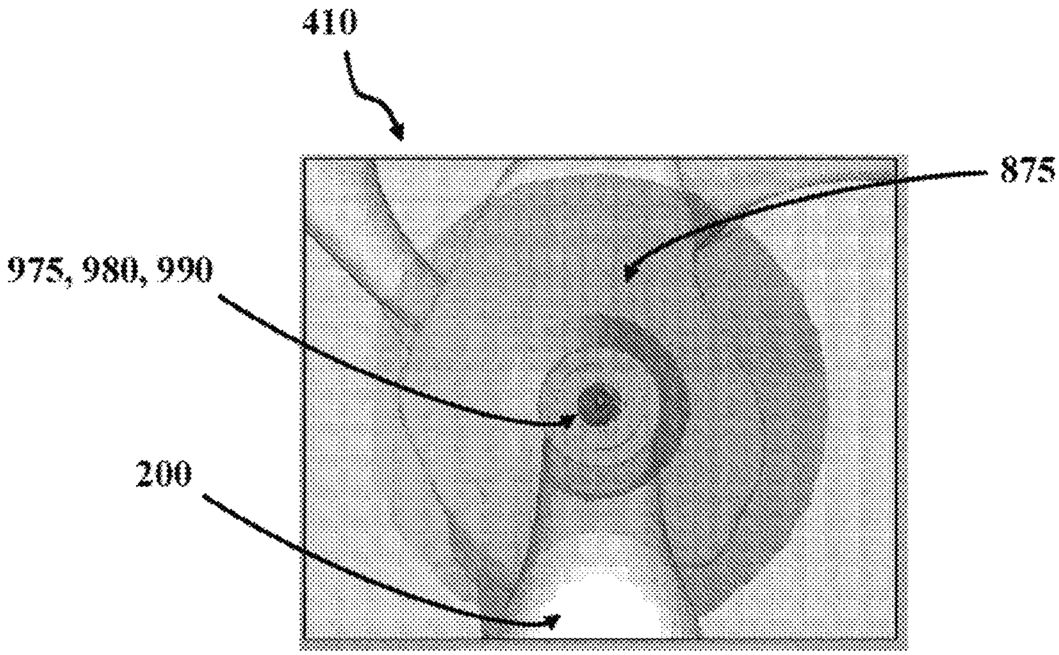

In embodiments in which a K-Wire is used for the shoulder arthroplasty, a K-Wire Guide 975 as shown in FIG. 26 may be attached to the handheld surgical tool 200. The user can insert the K-Wire 980 into the K-Wire Guide 975 and position the K-Wire 980 on the K-Wire insertion point 990. The visual display 410 can display an animation of the real-time K-Wire Guide 975 position relative to the patient's glenoid 875, and a depiction of the desired K-Wire trajectory. The user can also utilize feedback from the animation to move the K-Wire Guide 975 into the correct trajectory. The GUI module can indicate, for example by sound or color or other graphical means, when the K-Wire Guide 975 is being held within a predefined angular tolerance from the desired trajectory (see FIGS. 27A and 27B). The user can drill the K-Wire into the patient's glenoid 875 while the K-Wire Guide 975 is being held in the correct trajectory as indicated by the GUI module (see FIG. 27).

The above-described systems and methods are given for clearness of understanding only, and alternative computer-aided surgical navigation systems and methods are within the scope of this disclosure. For example, the systems and methods may be carried out for surgical procedures besides the illustrated hip arthroplasty and shoulder arthroplasty procedures.

Detailed embodiments of the present systems and methods are disclosed herein; however, it is to be understood that the disclosed embodiments are merely illustrative and that the systems and methods may be embodied in various forms. In addition, each of the examples given in connection with the various embodiments of the systems and methods are intended to be illustrative, and not restrictive.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where systems are described as including components, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

The invention claimed is:

1. A method of implanting a prosthesis in a patient undergoing a joint arthroplasty using a surgical navigation system, wherein the surgical navigation system comprises:
- a handheld surgical tool with computer-aided navigation, wherein the handheld surgical tool comprises a handle and an instrument shaft;
- a graphical user interface (GUI) module executed by a computing device, wherein the GUI module comprises a visual display that is configured to indicate a location of the handheld surgical tool; and
- an imaging device comprising a three-dimensional scanning tool;
- the method comprising:
  - exposing a joint of the joint arthroplasty;
  - placing one or more markers on anatomical features of the joint;
  - generating a three-dimensional surface or model of the anatomical features and the one or more markers;
  - engaging the handheld surgical tool with the one or more markers and recording an orientation of the handheld surgical tool during the engagement;
  - registering the orientation of the handheld surgical tool relative to an orientation of the joint;
  - displaying the three-dimensional surface or model, the orientation of the handheld surgical tool and a predetermined target orientation for the handheld surgical tool, on the visual display; and
  - implanting the prosthesis using the handheld surgical tool and the visual display, wherein the orientation of the handheld surgical tool is adjusted according to the predetermined target orientation for the handheld surgical tool.

2. The method of claim 1, further comprising the step of, after the placing one or more markers step, imaging the anatomical features of the joint and the one or more markers using the three-dimensional scanning tool, wherein the three-dimensional scanning tool captures data corresponding to a shape and surface of bone on which the one or more markers are located, as well as a location and orientation of the one or more markers, wherein the step of generating the three-dimensional surface or model of the anatomy and the one or more markers is performed with the captured data.

3. The method of claim 1, wherein the one or more markers comprise a first marker placed on a pelvis and a second marker placed on a femur.

4. The method of claim 1, further comprising calculating relevant orientations and distances with regards to the patient's anatomy based upon the three-dimensional surface or model.

5. The method of claim 1, wherein the three-dimensional scanning tool is used to obtain a single point cloud file in which the one or more markers are visible.

6. The method of claim 5, further comprising running a point cloud matching algorithm on the three-dimensional surface or model to identify a location and orientation of each marker.

7. The method of claim 1, wherein the one or more markers each have a unique shape and a marker engager attached to the handheld surgical tool has a complementary shape, such that the one or more markers and the marker engager can mate in a single orientation.

8. A method of implanting a prosthesis in a patient undergoing a joint arthroplasty using a surgical navigation system, wherein the surgical navigation system comprises:
- a handheld surgical tool with computer-aided navigation, wherein the handheld surgical tool comprises a handle and an instrument shaft;
- a graphical user interface (GUI) module executed by a computing device, wherein the GUI module comprises the computing device and a visual display that is configured to indicate a location of the handheld surgical tool; and
- an imaging device comprising a three-dimensional scanning tool;
- the method comprising:
  - exposing a joint of the joint arthroplasty;
  - recording an image data of anatomy of the joint, or a portion thereof, and one or more markers placed on the joint using the three-dimensional scanning tool;
  - generating a three-dimensional surface or model of the anatomy of the joint, or the portion thereof, and the one or more markers using the GUI module;
  - engaging the handheld surgical tool with one or more anatomic features on the joint and recording an orientation of the handheld surgical tool during the engagement;
  - registering the orientation of the handheld surgical tool relative to an orientation of the joint;
  - displaying the three-dimensional surface or model together with the orientation of the handheld surgical tool, and a predetermined target orientation for the handheld surgical tool, on the visual display; and
  - implanting the prosthesis using the handheld surgical tool and the visual display, wherein the orientation of the handheld surgical tool is adjusted according to the predetermined target orientation for the handheld surgical tool.

9. The method of claim 8, wherein the handle comprises a processor and a sensor unit.

10. The method of claim 9, wherein the sensor unit comprises a 3-axis accelerometer, a 3-axis rate gyroscope, a 3-axis magnetometer, or a combination thereof.

11. The method of claim 9, wherein the sensor unit is configured to generate orientational data of the handheld surgical tool, and the processor or the computing device is configured to determine, based on the orientational data, the orientation of the handheld surgical tool and compare the orientation of handheld surgical tool with at least one preset target orientation.

12. The method of claim 11, wherein the visual display is configured to indicate a deviation of the orientation of the handheld surgical tool from the at least one preset target orientation.

13. The method of claim 8, further comprising generating a three-dimensional image or contour of a surface of the patient's anatomy or a portion thereof for display in conjunction with an indication of the location of the handheld surgical tool.

14. The method of claim 8, wherein the joint arthroplasty is a hip arthroplasty, knee arthroplasty, or shoulder arthroplasty.

15. The method of claim 8, wherein the three-dimensional scanning tool captures data corresponding to a shape and surface of bone on which the one or more markers are located, as well as a location and orientation of the one or more markers, wherein the three-dimensional scanning tool captures data corresponding to a shape and surface of bone on which the one or more markers are located, as well as a location and orientation of the one or more markers, and wherein the step of generating the three-dimensional surface or model is performed with the captured data.

16. The method of claim 8, wherein the one or more markers comprise a first marker placed on a pelvis and a second marker placed on a femur.

17. The method of claim 8, further comprising calculating relevant orientations and distances with regards to the patient's anatomy based upon the three-dimensional surface or model.

18. The method of claim 8, wherein the three-dimensional scanning tool is used to obtain a single point cloud file in which the one or more markers are visible.

19. The method of claim 8, wherein the method further comprises the step of running a point cloud matching algorithm on the three-dimensional surface or model to identify a location and orientation of each marker.

20. The method of claim 8, wherein the one or more markers each have a unique shape and a marker engager attached to the handheld surgical tool has a complementary shape, such that the one or more markers and the marker engager can mate in a single orientation.

* * * * *